United States Patent
Palfenier et al.

(10) Patent No.: US 6,647,350 B1
(45) Date of Patent: Nov. 11, 2003

(54) RADIOMETRIC TEMPERATURE MEASUREMENT SYSTEM

(75) Inventors: Ronald A. Palfenier, Oregon City, OR (US); Patrick J. Nystrom, Gresham, OR (US)

(73) Assignee: Exactus, Inc., Boca Raton, FL (US)

( * ) Notice: Subject to any disclaimer, the term of this patent is extended or adjusted under 35 U.S.C. 154(b) by 267 days.

(21) Appl. No.: 09/872,752

(22) Filed: Jun. 1, 2001

Related U.S. Application Data

(60) Provisional application No. 60/209,168, filed on Jun. 2, 2000, provisional application No. 60/209,074, filed on Jun. 2, 2000, provisional application No. 60/209,076, filed on Jun. 2, 2000, and provisional application No. 60/217,012, filed on Jul. 10, 2000.

(51) Int. Cl.[7] .......................... G01K 11/30; G06F 15/00
(52) U.S. Cl. ...................................................... 702/134
(58) Field of Search ................................ 702/130, 133, 702/134, 135; 374/2, 120, 121; 250/336.2, 339.04, 339.01, 338.4

(56) References Cited

U.S. PATENT DOCUMENTS

| | | | |
|---|---|---|---|
| 1,475,365 A | | 11/1923 | Schueler et al. |
| 1,639,534 A | | 8/1927 | Ruben |
| 2,709,367 A | | 5/1955 | Bohnet |
| 3,626,758 A | | 12/1971 | Stewart et al. |
| 4,075,493 A | | 2/1978 | Wickersheim |
| 4,348,110 A | | 9/1982 | Ito |
| 4,576,486 A | | 3/1986 | Dils |
| 4,750,139 A | | 6/1988 | Dils |
| 4,845,647 A | | 7/1989 | Dils et al. |
| 4,956,538 A | | 9/1990 | Moslehi |
| 5,154,512 A | | 10/1992 | Scheitinger et al. |
| 5,203,631 A | * | 4/1993 | Delfino et al. ............... 374/123 |
| 5,490,728 A | * | 2/1996 | Schietinger et al. ........... 374/7 |
| 5,713,666 A | * | 2/1998 | Seelin et al. ................. 374/126 |
| 5,717,608 A | | 2/1998 | Jensen |
| 5,730,527 A | * | 3/1998 | Takayama et al. ........... 374/131 |
| 5,815,410 A | | 9/1998 | Heinke et al. |
| 5,822,222 A | * | 10/1998 | Kaplinsky et al. .......... 702/134 |
| 5,897,610 A | | 4/1999 | Jensen |
| 5,993,059 A | * | 11/1999 | O'Neill et al. ............... 374/126 |
| 6,007,241 A | | 12/1999 | Yam et al. |
| 6,062,729 A | * | 5/2000 | Ni et al. ...................... 374/161 |
| 6,128,325 A | * | 10/2000 | Goldstein et al. ............. 372/73 |
| 6,179,466 B1 | * | 1/2001 | Peuse et al. ................. 374/128 |
| 6,183,130 B1 | * | 2/2001 | Adams et al. ............... 374/131 |
| 6,299,346 B1 | * | 10/2001 | Ish-Shalom et al. ........ 374/126 |
| 6,325,536 B1 | * | 12/2001 | Renken et al. ............... 374/161 |
| 6,345,909 B1 | * | 2/2002 | Yam .............................. 374/2 |
| 2002/0066859 A1 | * | 6/2002 | Ino et al. ................ 250/339.04 |

OTHER PUBLICATIONS

"Optical Pyrometry Begins to Fulfill its Promise," Alexander Braun, Semiconductor International, Mar. 1998, pp. 1 and 2.
"A New Detector for IRLED Light," Russ Dahl and Michael Allen, reprinted from SENSORS Magazine, Dec. 1996, 4 pp.

* cited by examiner

*Primary Examiner*—John Barlow
*Assistant Examiner*—Demetrius Pretlow
(74) *Attorney, Agent, or Firm*—Stoel Rives LLP

(57) ABSTRACT

A radiometric system (10) typically used in semiconductor wafer processing has reduced optical losses, improved wavelength selectivity, improved signal to noise, and improved signal processing to achieve wafer temperature measurements from about 10° C. to 4,000° C. A YAG rod collection optic (12) directly couples specimen radiation (14) to a filter (18) and photo detector (20). The filter determines which radiation wavelengths are measured, and optionally includes a hot/cold mirror surface (22) for reflecting undesired radiation wavelengths back to the specimen. The detector is formed from doped GaAlAs having a peaked response near 900 nm. A signal processor (28) converts the signal into a temperature reading.

27 Claims, 12 Drawing Sheets

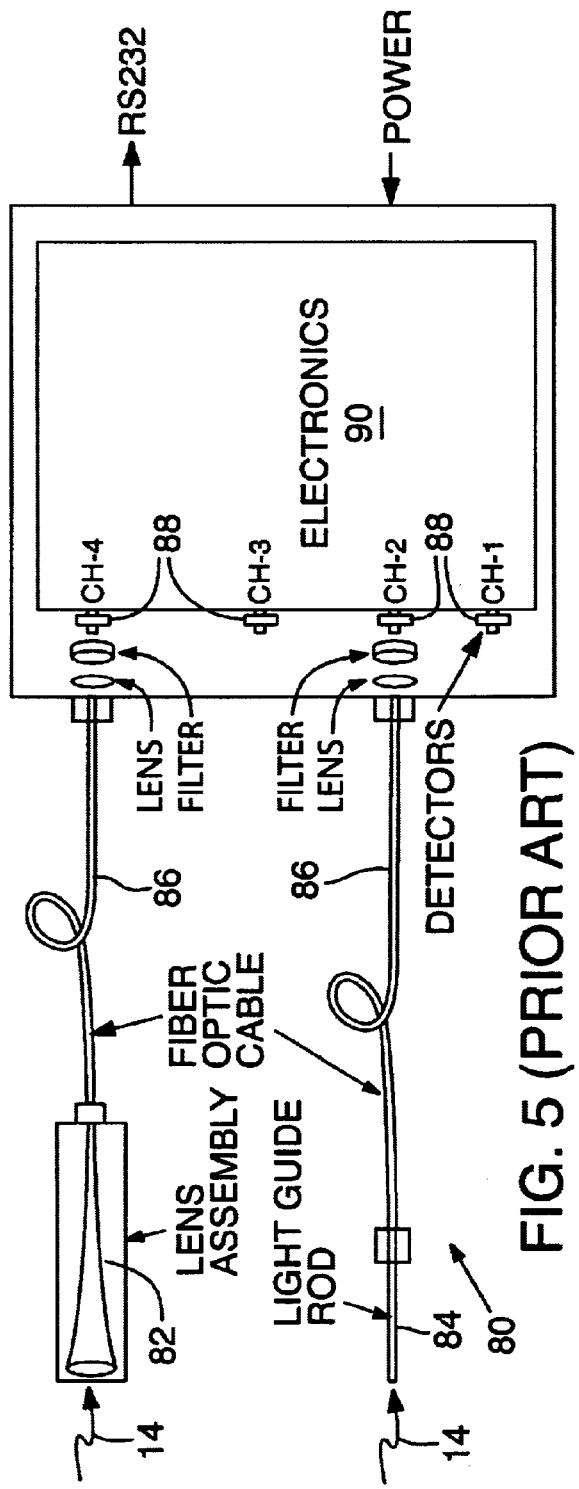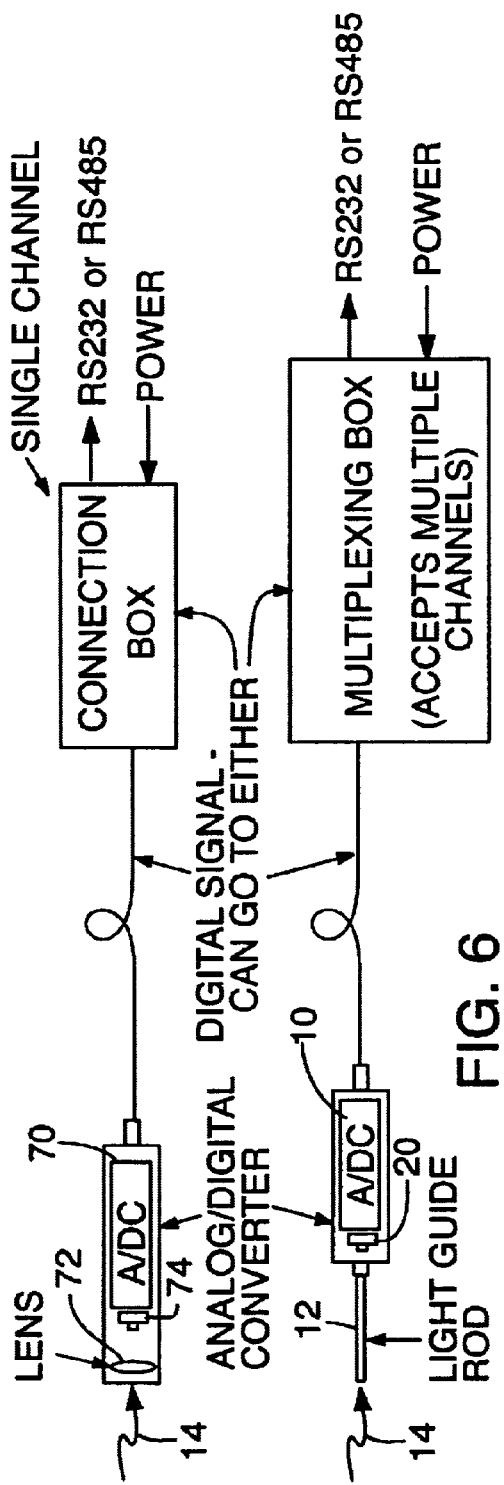

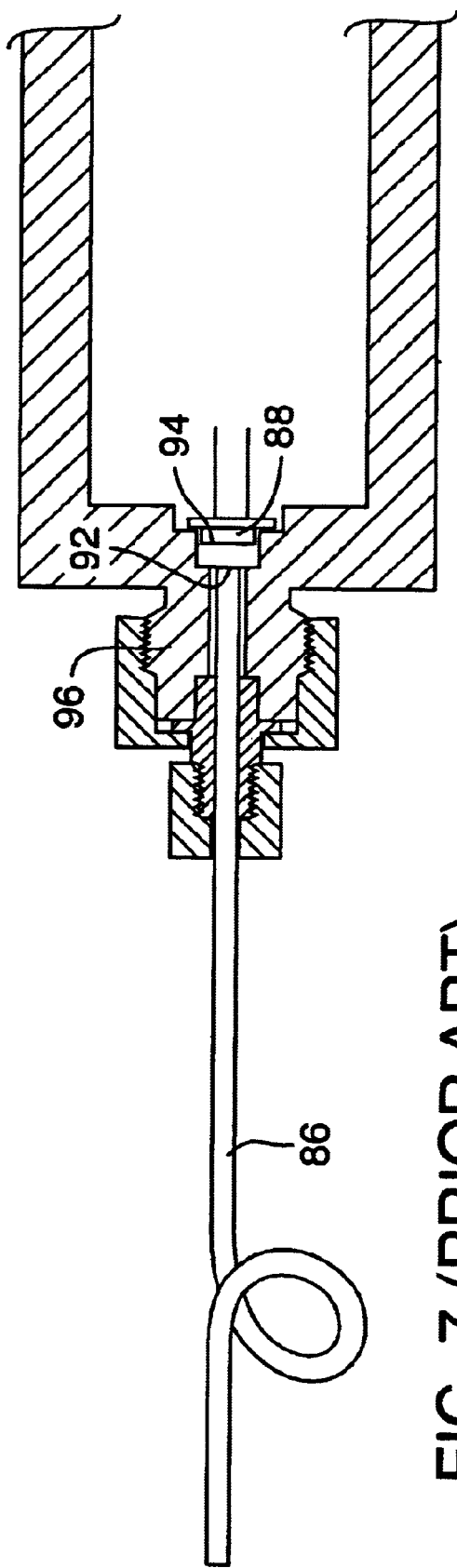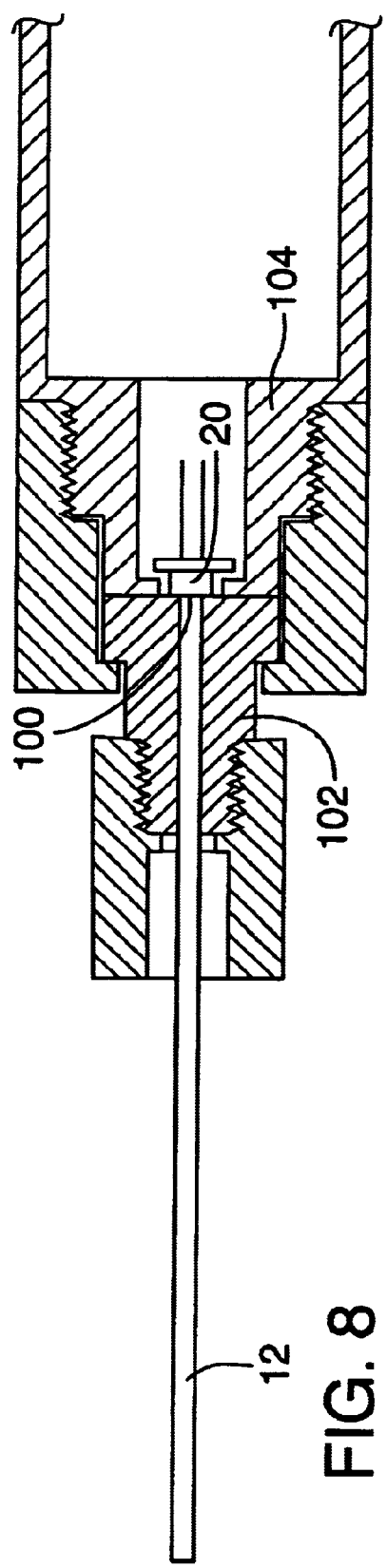
FIG. 7 (PRIOR ART)
FIG. 8

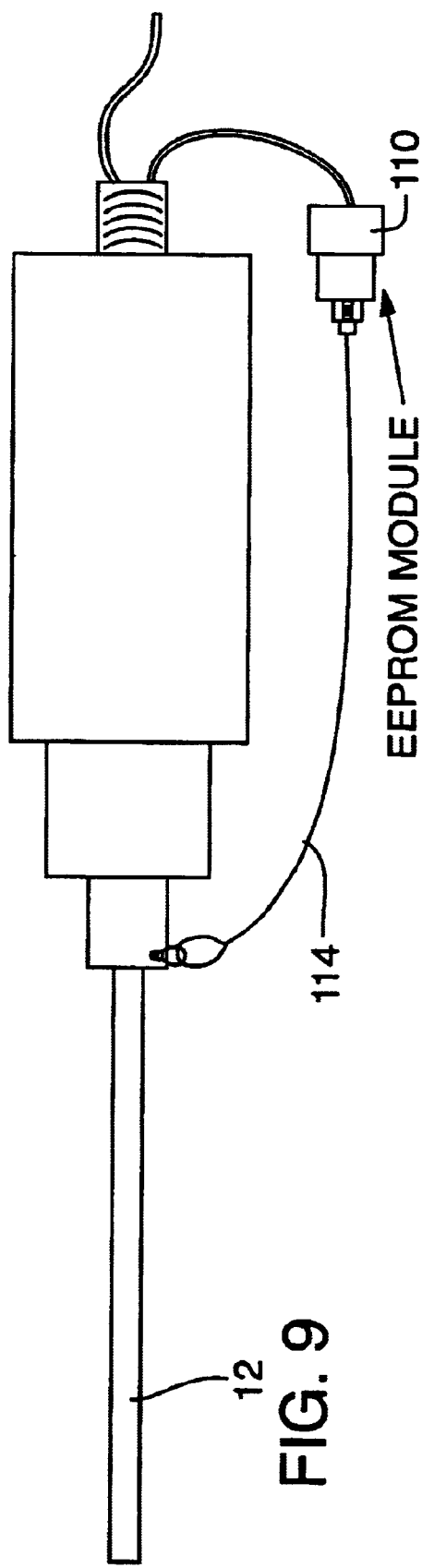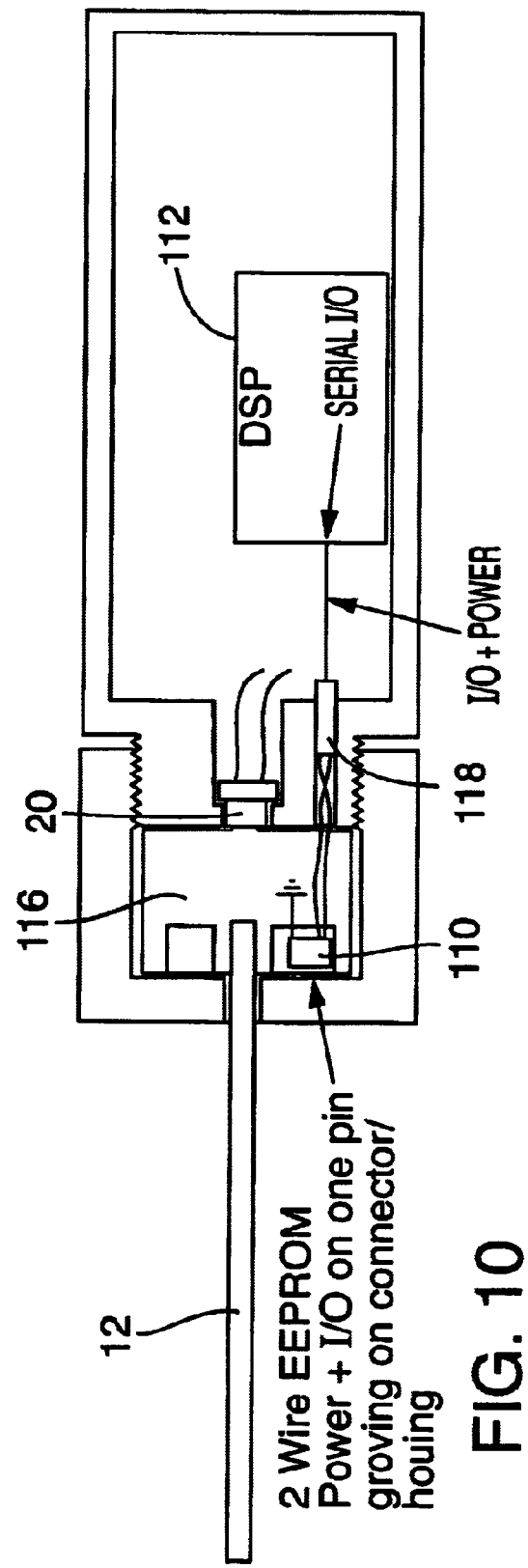
FIG. 9
FIG. 10
2 Wire EEPROM
Power + I/O on one pin
groving on connector/
houing

RADIOMETRIC TEMPERATURE MEASUREMENT SYSTEM

RELATED APPLICATIONS

This application claims priority from U.S. Provisional Application Nos. 60/209,168; 60/209,074; and 60/209,076; all filed Jun. 2, 2000, and No. 60/217,012, filed Jul. 10, 2000.

FEDERALLY SPONSORED RESEARCH OR DEVELOPMENT

Not Applicable

TECHNICAL FIELD

This invention relates to radiometric temperature measurement systems (also known as "pyrometers") and more particularly to a pyrometer system having improved low temperature measurement sensitivity for determining a surface temperature of a semiconductor wafer or an object without contacting its surface. The pyrometer system employs a relationship between an intensity of the radiation and a source temperature as defined by the Planck equation, which shows that the radiation emitted by any object is a function of its temperature, emissivity, and the measurement wavelength.

BACKGROUND OF THE INVENTION

Pyrometer-based temperature measurement systems have a long development history. For example, even before 1930, U.S. Pat. Nos. 1,318,516; 1,475,365; and 1,639,534 all described early pyrometers. In 1933, U.S. Pat. No. 1,894,109 to Marcellus described a pyrometer employing an optical "lightpipe." In 1955, U.S. Pat. No. 2,709,367 to Bohnet described a pyrometer in which sapphire and curved sapphire lightpipes are used in collection optics. In 1971, U.S. Pat. No. 3,626,758 to Stewart described using quartz and sapphire lightpipes with a blackbody sensor tip. Then in 1978, U.S. Pat. No. 4,075,493 to Wickersheim described a modern flexible fiber optic thermometer.

In the 1980s, U.S. Pat. No. 4,348,110 to Ito described electronic improvements to pyrometers, such as an integrating photo-detector output circuit. Then U.S. Pat. Nos. 4,576,486, 4,750,139, and 4,845,647, all to Dils, described further improvements to electronics, fiber-optics, sapphire rods, and blackbody emission temperature measurements.

In the 1990s, many patents issued that describe the use of pyrometers in semiconductor processing. For example, in 1990, U.S. Pat. No. 4,956,538 to Moslehi described using fiber optic lightpipes for wafer temperature measurements in rapid thermal processing ("RTP") applications. In 1992, U.S. Pat. No. 5,154,512 to Schietinger described using a fiber optic thermometer with wavelength selective mirrors and modulated light to measure semiconductor wafer temperatures. In 1998, U.S. Pat. No. 5,717,608 to Jenson described using an integrating amplifier chip and fiber-optics to measure semiconductor wafer temperatures, and U.S. Pat. No. 5,815,410 to Heinke described an infrared ("IR") sensing thermometer using an integrating amplifier. Then in 1999, U.S. Pat. No. 5,897,610 to Jensen described the benefits of cooling pyrometers, and U.S. Pat. No. 6,007,241 to Yam described yet another fiber optic pyrometer for measuring semiconductor wafer temperatures.

As one can see from these prior patents, pyrometer systems are commonly used for measuring the temperature of semiconductor silicon wafers housed within a process chamber while forming integrated circuits ("ICs") on the wafer. Virtually every process step in silicon wafer fabrication depends on the measurement and control of wafer temperature. As wafer sizes increase and the critical dimension of very large scale ICs scales deeper into the submicron range, the requirements for wafer-to-wafer temperature repeatability during processing become ever more demanding.

Processes such as physical vapor deposition ("PVD"), high-density plasma chemical vapor deposition ("HDP-CVD"), epitaxy, and RTP can be improved if the wafer temperature is accurately measured and controlled during processing. In RTP there is a special importance to temperature monitoring because of the high temperatures and the importance of tightly controlling the thermal budget, as is also the case for Chemical Mechanical Polishing ("CMP") and Etch processes.

As wafer sizes increase, the cost of each wafer increases geometrically, and the importance of high quality in-process temperature monitoring increases accordingly. Inadequate wafer temperature control during processing reduces fabrication yields and directly translates to lost revenues.

In addition to conventional pyrometry, the most common in-situ temperature sensing techniques employed by semiconductor processing wafer fabs and foundries also includes thermocouples and advanced pyrometry.

Thermocouples are easy to use, but their reliability and accuracy are highly questionable. Thermocouples are only accurate when the wafer is in thermal equilibrium with its surroundings and the thermocouple is contacting or embedded in that environment. Otherwise, the thermocouple reading might be far from the correct wafer temperature. For example, in PVD applications, while the thermocouple embedded in the heated chuck provides a temperature measurement that resembles that of the wafer, there are large offsets between the wafer and the thermocouple. These offsets are a function of gas pressure and heat transfer.

In conventional optical pyrometry, a pyrometer deduces the wafer temperature from the intensity of radiation emitted by the wafer. The pyrometer typically collects the radiation from the wafer through an interface employing a lens or a quartz or sapphire rod. Such interfaces have been used with PVD, HDP-CVD, RTP, Etch, and rapid thermal chemical vapor deposition ("RTCVD"). While conventional optical pyrometers are often superior to the use of thermocouples, there are measurement inaccuracy problems caused by the processing environment, such as background light, wafer transmission, emissivity, and signal-to-noise ratio problems that cannot be ignored.

Advanced pyrometry offers some satisfactory temperature monitoring solutions for semiconductor wafer production applications. "*Optical Pyrometry Begins to Fulfill its Promise*," by Braun, Semiconductor International, March 1998, describes advanced pyrometry methods that overcome some limitations of conventional pyrometry. As such, optical pyrometers and fiber optic thermometers employing the Planck Equation are now commonly used for in-situ semiconductor wafer measurement. However, numerous problems and limitations are still encountered when measuring wafer temperature using "Planck" radiation (light) emitted by the wafer. There are three problems in particular when measuring wafers at temperatures below about 400° C.: 1) minimal signal levels generated by the photo detector (as small as 1E-16 amps) (see FIG. 19) because the very small amount of radiation emitted by the wafer; 2) the wafer is semi-transparent at low temperatures and long wavelengths (greater then 1,700 nm); and 3) the background light is often larger than the emitted wafer signal and causes large errors when it enters the collection optics.

What is still needed, therefore, is an advanced pyrometer system that provides accurate and repeatable temperature measurements of an object, such as a semiconductor wafer, down to about room temperature without contacting the object being measured.

SUMMARY OF THE INVENTION

An object of this invention is, therefore, to provide an apparatus and a method for performing non-contacting temperature measurements of target media.

Another object of this invention is to provide an advanced pyrometer system capable of measuring semiconductor wafer temperatures down to about room temperature.

A further object of this invention is to provide an advanced pyrometer system having high temperature measurement accuracy and repeatability.

Still another object of this invention is to provide an advanced pyrometer system that is more compact than prior advanced pyrometer systems.

An advanced pyrometer system of this invention has reduced optical losses, better background radiation blocking, improved signal-to-noise ratio, and improved signal processing to achieve improved accuracy and temperature measurement capabilities ranging from about 10° C. to about 4,000° C.

The system includes collection optics that acquire emitted radiation from a hot specimen and directly couples it to an optional filter and a photo detector. The collection optics may include lens systems, optic lightpipes, and flexible fiber optics. The preferred collection optic is a yttrium-aluminum-garnet ("YAG") light guide rod. The filter is wavelength-selective to determine which radiation wavelengths are measured, and optionally includes a hot/cold mirror surface for reflecting undesired radiation wavelengths back to the specimen. The photo detectors are formed from silicon, InGaAs or, preferably, doped GaAlAs having a narrow bandpass detection characteristic centered around 900 nm. The doped GaAlAs detector allows eliminating the optical filter if additional detection sensitivity is required. Also, light at wide angles has less effect on the wavelength sensitivity of the GaAlAs detector.

The system further includes an amplifier that acquires and conditions signals as small as $10^{-16}$ amps (see FIG. 19) for detection and measurement. A signal processor converts the amplified signal into a temperature reading. This processing is a combination of electrical signal conditioning, analog-to-digital conversion, correction factors, and software algorithms, including the Planck equation. The resulting processed signal is a high-speed digital signal that is suitable for viewing with Windows®- or host computer-based user software.

Additional objects and advantages of this invention will be apparent from the following detailed description of preferred embodiments thereof that proceed with reference to the accompanying drawings.

BRIEF DESCRIPTION OF THE DRAWINGS

FIG. 5 is a simplified pictorial view of a prior art pyrometer system employing optical fiber cables to couple emitted radiation to detectors.

FIG. 6 is a simplified pictorial view of a pyrometer system of this invention employing direct coupling of emitted radiation to detectors.

FIG. 7 is a sectional side view of a prior art light guide rod and detector mounting system in which the optical faces of the light guide rod and detector are recessed within threaded housings making cleaning difficult.

FIG. 8 is a sectional side view of a light guide rod and detector mounting system of this invention in which the optical faces of the light guide rod and detector are flush to the edges of their respective housings and, therefore, easy to clean.

FIG. 9 is a pictorial side view of a pyrometer showing a freestanding embodiment of an electrically erasable programmable read-only memory ("EEPROM") calibration key of this invention.

FIG. 10 is a pictorial side view of a pyrometer showing an integrated embodiment of the EEPROM calibration key of this invention.

DETAILED DESCRIPTION OF PREFERRED EMBODIMENTS

Figure 1:
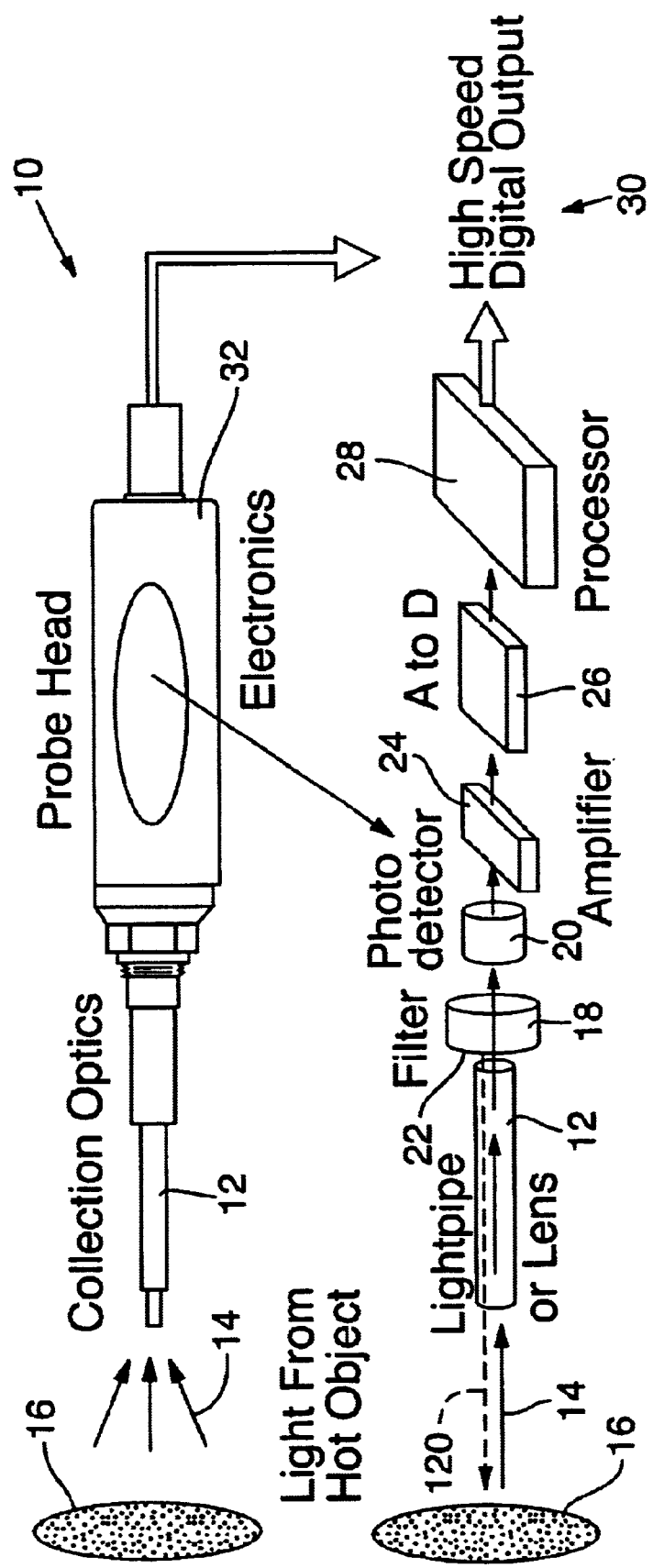
FIG. 1 is a combined pictorial and corresponding schematic block diagram of an pyrometer system of this invention.

FIG. 1 shows a radiometric system 10 of this invention, which includes collection optics 12 for acquiring emitted radiation 14 from a target medium, such as an object 16. Collection optics 12 direct radiation 14 to an optional wavelength selective filter 18 and a photo detector 20. Collection optics 12 may alternatively include rigid or flexible fiber optic light pipes and/or a lens system for measuring the temperature of predetermined areas on object 16. The target medium may include gases, plasmas, heat sources, and other non-solid target media.

Optional wavelength selective filter 18 selects which wavelengths of radiation 14 are measured. A preferred embodiment of filter 18 includes a hot/cold mirror surface 22 for reflecting unneeded wavelengths of radiation 14 back toward object 16. Skilled workers will recognize that filter 18 and hot/cold mirror surface 22 should be housed to maintain them in a clean and dry condition.

Figure 19:
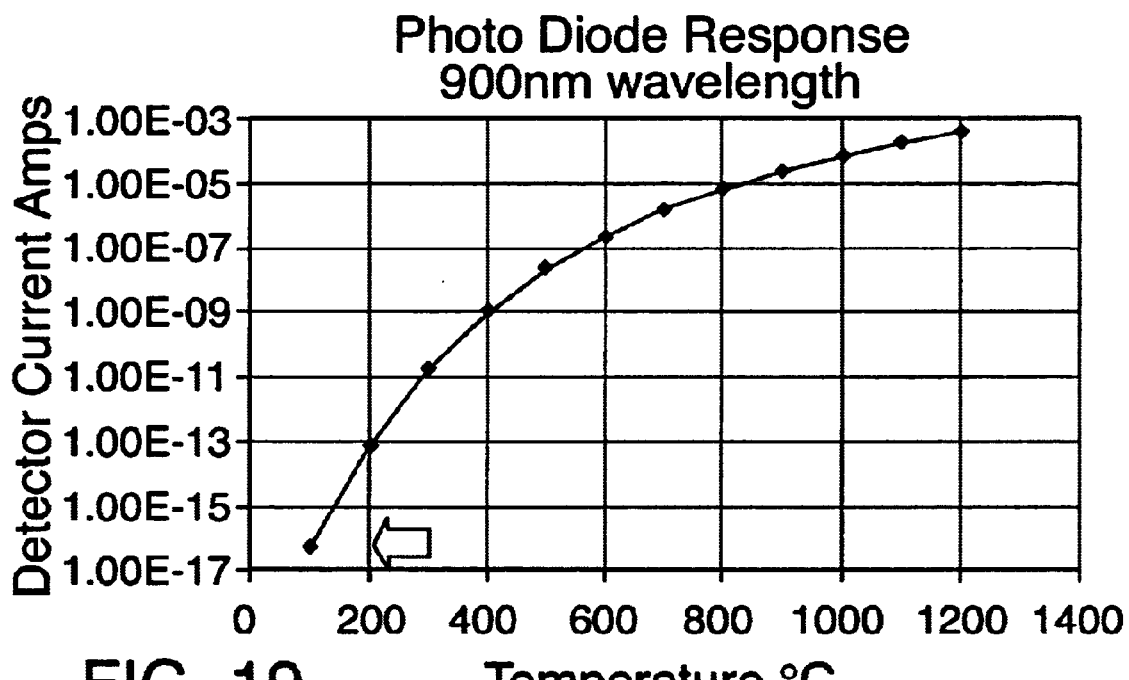
FIG. 19 is a graph representing photo detector current at a 900 nm wavelength as a function of temperature.

Photo detector 20 converts radiation 14 into an electrical signal. Photo detector 20 can be a high efficiency solid-state detector device formed from silicon, InGaAs and, preferably, a specially doped GaAlAs material having a narrow bandpass detection characteristic centered around 900 nm. Detector 20 is described in more detail with reference to FIGS. 15, 16, and 19.

Radiometric system 10 further includes an amplifier 24 that receives the small electrical signal from photo detector 20 and amplifies the signal to a level suitable for further processing. Amplifier 24 of this invention allows measuring electrical signals as small as $10^{-16}$ amps (see FIG. 19).

Radiometric system 10 further includes an analog-to-digital converter ("ADC") 26 for converting the amplified electrical signal into a digital signal and a signal processor 28 for processing the digital signal into a temperature reading. The processing includes software algorithms employing the Planck equation.

Radiometric system 10 generates a high-speed digital output signal 30, which can be viewed as temperature measurements on a personal or host computer running conventional user software or, preferably, a Windows®-based user software product named TemperaSure™, which is available from Engelhard Corporation, located in Fremont, Calif.

Radiometric system 10 further includes a generally tubular housing 32 that encloses at least photo detector 20, amplifier 24, ADC 26, and signal processor 28. Housing 32 is preferably at least about 2.54 cm (1 inch) in diameter and at least about 10.16 cm (4 inches) long. Of course, the shape and dimensions of housing 32 may vary to suit different applications.

Figure 2:
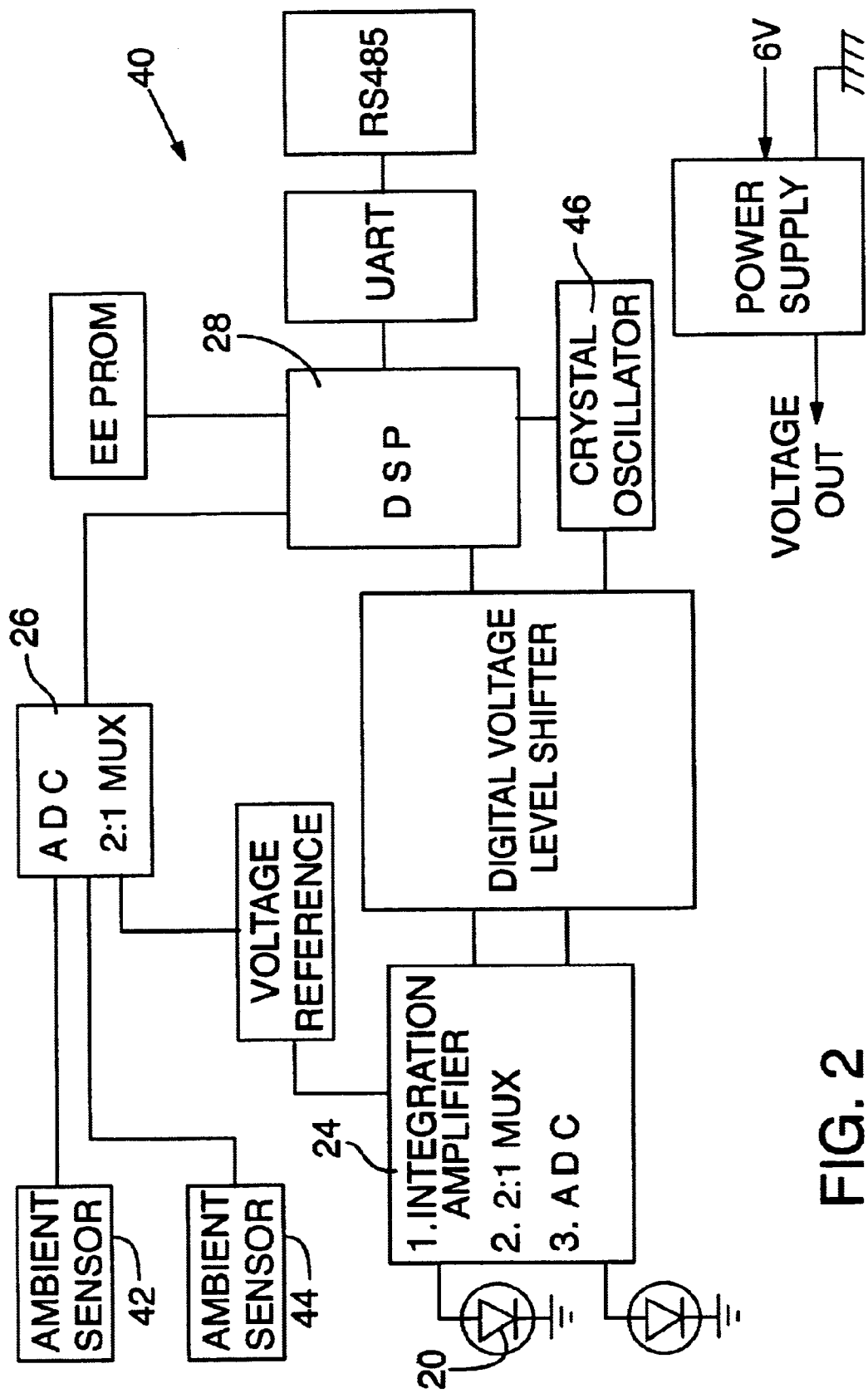
FIG. 2 is a simplified electrical block diagram of the electronic circuitry portion of the pyrometer system of this invention.

FIG. 2 shows a block diagram of electronic circuitry 40 portions of radiometric system 10, which circuitry is preferably included on a printed circuit board (not shown) that fits within housing 32. Electronic circuitry 40 utilizes significantly smaller components and arrays them in a highly compact format such that the overall instrument size is reduced dramatically from prior pyrometers. This form factor enables direct coupling of photo detector 20 and electronic circuitry 40 to collection optics 12 and, therefore, eliminates the undesirable fiber cable often found in prior optical thermometers. Eliminating the fiber cable in semiconductor temperature measurement applications reduces optical losses and signal variations.

Electronic circuitry 40 preferably includes photo detector 20 and an array of IC chips for amplifying and integrating the electrical signal generated by photo detector 20. Electronic circuitry further includes two or more temperature sensors 42 and 44 to monitor ambient temperatures of components, such as photo detector 20, amplifier 24, wavelength selective filter 18, and a timing circuit 46.

Compensating target temperatures based on information gained from sensors 42 and 44 accounts for deviations in component performance having differing temperature-dependent physical behaviors. For example, amplifier 24 gain changes with temperature as do the characteristics of photo detectors, analog to digital converters, timing oscillator crystals, and reference voltage or current sources. It is also beneficial to use an internal temperature sensor to monitor and compensate for the temperature of objects within the pyrometer system that occupy any part of the field of view ("FOV") of the photo detector.

Electronic circuitry 40, in combination with the techniques described herein, increases the signal-to-noise ratio of radiometric system 10 and allows temperature measurements to be made down to about 10° C. by measuring object emissions at or near 1,650 nm, and down to about 170° C. by measuring object emissions at slightly below 1,000 nm. These conditions provide signal levels that have heretofore been too weak to measure accurately.

By comparison, the temperature measuring limits of prior optical radiometers operating at wavelengths less than 1,650 nanometers, with ±5 degrees of noise, and a 1 Hz sampling bandwidth, is approximately 50° C. with a cooled/un-cooled indium gallium arsenide detector ("InGaAs"); or about 300° C. with a cooled/un-cooled silicon detector at 900 nm.

It should be noted that while the minimum temperature measuring limit is reduced by only a factor of two for the InGaAs detector and by a factor of about 1.6 for the silicon detector, the signal reduction at the detector is approximately a factor of 50 for the InGaAs detector and a factor of 3,000 for the equivalent silicon detector. This invention has enabled these minimum temperature measurement reductions through reducing optical losses, reducing or eliminating factors that cause signal level variations, and electronic signal processing improvements.

Figure 3:
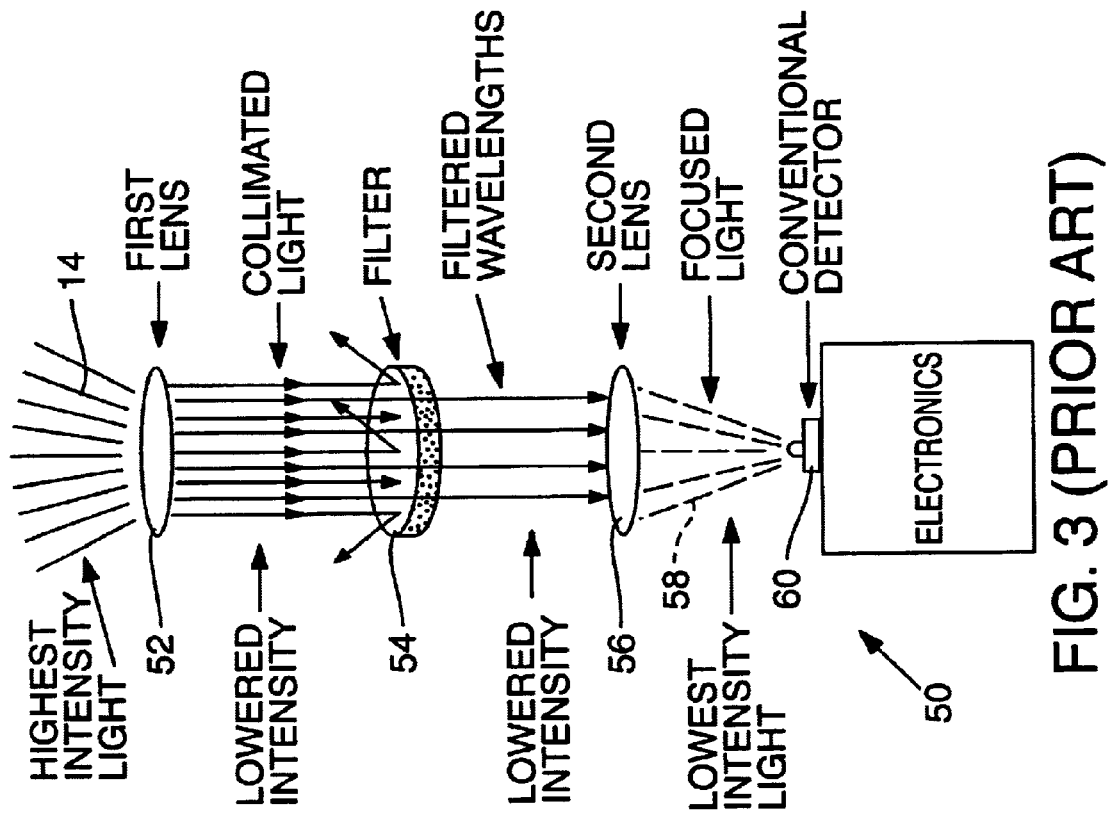
FIG. 3 is a simplified pictorial view of a prior art optical pyrometer employing a first lens for collimating radiation through a filter and a second lens for focusing the filtered radiation on a silicon detector.

Regarding improvements that reduce optical losses, FIG. 3 shows a prior art optical pyrometer 50 employing a first lens 52 for collimating radiation 14 through a wavelength selective filter 54 and a second lens 56 for focusing filtered radiation 58 on a conventional silicon detector 60. Wavelength selective filter 54 transmits a desired radiation wavelength and blocks unwanted wavelengths. For example, long wavelength blocking filters block light at long wavelengths while transmitting short wavelengths of light. Unfortunately, filters do not transmit the desired radiation wavelengths with 100 percent efficiency, which causes optical losses that adversely affect the measurement system sensitivity. Moreover, filters work best with collimated light, which usually requires multiple lenses to collimate the light through the filter and then focus it on the detector. The multiple lenses further reduce the amount of light that reaches the detector.

Figure 4:
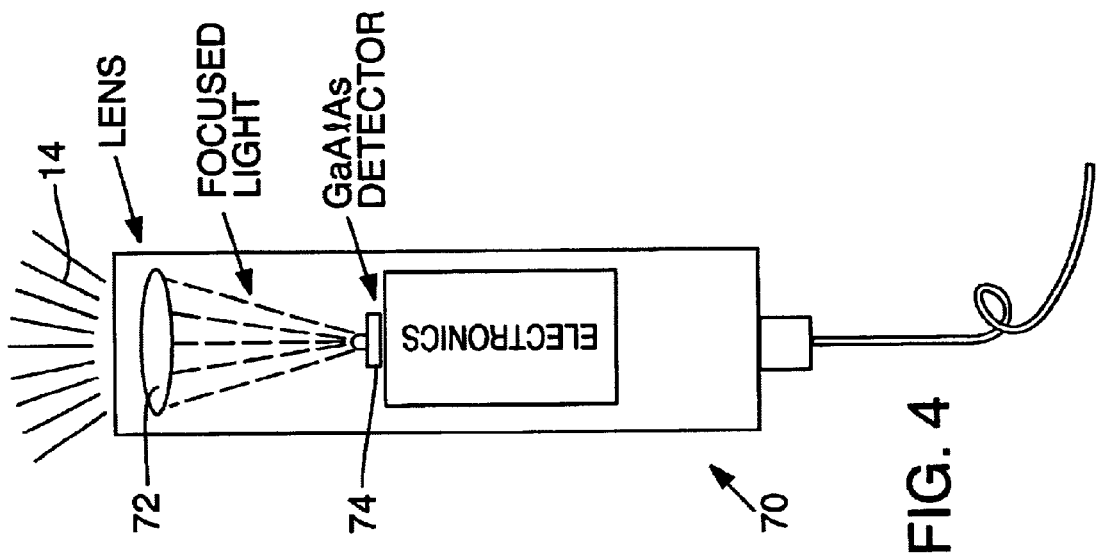
FIG. 4 is a simplified pictorial view of an optical pyrometer of this invention employing a single lens for focusing radiation on a wavelength selective GaAlAs detector.

In contrast, FIG. 4 shows an optical pyrometer 70 of this invention that employs a single lens 72 for focusing radiation 14 on a wavelength selective GaAlAs detector 74 of this invention. The wavelength selective filtering achieved by GaAlAs detector 74 has a rapidly diminishing response as wavelength increases, enabling a measurement system having increased sensitivity because the losses associated with filter 54 and second lens 56 are eliminated. Also the angled light does not effect the wavelength sensitivity of the GaAlAs detector.

Miniaturization of the detector/electronics system and direct coupling to the light capturing source further increase the measurement sensitivity of the pyrometers of this invention.

FIG. 5 shows a typical prior art pyrometer system 80 that employs a lens assembly 82 or a quartz or sapphire light guide rod 84 for collecting radiation 14 and propagating it onto an optical fiber or fiber bundle 86 for conduction to a detector 88. Light guide rod 84 or lens assembly 82 interfaces with the high temperature environment of the object. Optical fiber 86 isolates detector 88 and associated electronics 90 from electrical noise and heat and provides mechanical flexibility for placing detector(s) 88 in a convenient location. While this arrangement provides mechanical convenience, the following factors associated with using optical fibers 86 in semiconductor applications reduce their ability to accurately transmit radiation 14 to detector(s) 88:

- If a single flexible fiber is employed to propagate radiation 14 from light guide rod (lightpipe) 84 to detector 88, then there will be large (~80%) optical losses due to the difference in index of refraction and the fact that the flexible fiber is usually smaller in diameter than the lightpipe. If, instead, a fiber bundle is employed to propagate the radiation from the light guide rod (lightpipe) to the detector, significant loss of optical signal strength will still result due to the mismatched index of refraction and the fill factor of the bundle (the spaces between fibers) being less than 100 percent.
- Because of the limited availability of glass types from which to make optical fiber 86, it is nearly impossible to achieve a numerical aperture that is equivalent to the index of refraction of light guide rod 84.
- Unless optical fiber 86 includes an antireflection coating, reflection losses will exist at the glass-to-air interfaces at the ends of optical fiber 86. The reflection losses are exacerbated if the index of refraction is raised in an attempt to capture all of the light from light guide rod 84.
- Because optical fiber 86 can only contain radiation that is traveling over a limited range of angles, radiation 14 that is captured by lens assembly 82 or light guide rod 84 and propagated into optical fiber 86 will have a variable loss if optical fiber 86 is flexed.
- As optical fiber 86 is heated or cooled, its transmission characteristics change causing transmitted signal variations.
- When employing an optical fiber cable, errors are easily introduced at both ends of the cable: first, through misalignment of the cable ends when they are connected to the light guide rod 84 and photo detector 88, and secondly due to imperfect cleaning of the two surfaces. Moreover, when optical fiber 86 is attached and removed from the radiation collection system or detector 88, alignment changes can occur causing variations in the transmitted light.

By way of comparison, FIG. 6 shows that in this invention, the losses and signal variations associated with optical fibers are eliminated by eliminating optical fiber(s) 86 and directly coupling detector 20 to light guide rod 12 and/or detector 74 to lens 72 of respective pyrometers 10 (FIG. 1) and 70 (FIG. 4). To accomplish this in a mechanically effective way, the detector and supporting electronics are miniaturized as shown in FIG. 1 to fit into space-constrained locations.

As the device geometry of ICs becomes ever smaller, the measurement of lower temperatures becomes more critical for these processes. As temperatures decrease, the amount of radiation emitted by the wafer also decreases. Therefore, the radiation transmission efficiency of light guide rods coupled to detectors become ever more critical to accurate temperature measurements.

Moreover, as the price of IC's decreases, extreme cost-reduction pressure has been placed on semiconductor equipment manufacturers. Given the high cost of sapphire, the current state-of-the-art material for fabricating light guide rods, alternative materials have long been sought after for making light guide rods.

Accordingly, this invention includes an improved light guide rod material for reducing the optical losses encountered when employing optical pyrometry in semiconductor processing applications. This improved material is formed of aluminum oxide crystals, the preferred type being YAG, which provides increased light transmission characteristics, resulting in improved low temperature measurement capabilities. A suitable alternative light guide rod material is yttrium aluminum perovskite ("YAP"). Recent processing improvements have allowed manufacturing YAG and YAP in rod lengths and form factors suitable for use in optical pyrometry applications.

YAG retains many of the benefits of sapphire, in that it is very similar in hardness (MOHS hardness of 8.2 vs. 9 for sapphire), melting point (1,965° C. vs. 2,050° C. for sapphire), and ability to withstand thermal shock. These unexpected benefits make YAG ideally suited for fabricating light guide rods 12 and 84 used in temperature sensing for semiconductor applications.

While YAG has been used for other optical applications such as in lasers, hitherto it could not be grown long enough and was usually doped, so it has never been considered as a potential light guide rod material. However, the increased demand for YAG for other applications resulted in major manufacturing advances, with producers now able to grow it in lengths up to one meter. This recent development and additional new research in non-doped YAG has led to the unexpected discovery of many properties that make YAG ideally suited for use in semiconductor applications. For example, when compared to sapphire, the YAG material:

- reduces optical losses because of its higher index of refraction and better crystal structure;
- reduces or eliminates factors which cause variations in the signal level due to lack of uniformity from light guide rod to light guide rod;
- is less affected by surface contamination;
- provides tighter machining tolerances;
- reduces the light guide rod's thermal conductivity; and
- as opposed to sapphire, YAG is easier to machine into round rods because of its crystal structure.

Regarding reduced optical losses, YAG has a higher refractive Index, resulting in better radiation transmission. When fabricating light guide rods, a ferrule is attached to the light guide rod as a means of securing the rod to the pyrometer. An O-ring is also typically attached to the rod to provide a seal between the rod and the wafer-processing chamber into which the rod is inserted. However, when these parts contact the rod, radiation can be scattered at the contact points. Care must be taken, therefore, in selecting materials with a high refractive index to prevent radiation from scattering at the contact points. Accordingly, only sapphire and quartz have been used in prior semiconductor applications. While these materials provide a high refractive index, a consistent problem (particularly with quartz) has been that radiation is still scattered at the ferrule and O-ring contact points, thus reducing the light guide rod's transmission capabilities.

An improvement therefore would be to employ a material having characteristics similar to sapphire or quartz but with a higher refractive index to reduce the amount of scattered radiation at the contact points. Because YAG has a higher refractive index (1.83 @ 632.8 nm) than sapphire or quartz, it is less sensitive to radiation losses at the contact points and is, therefore, ideally suited as an improved light guide rod material.

When fabricating light guide rods, it is important to obtain highly polished rod sides to prevent radiation from scattering out of the guide rod sides. Because quartz is a soft material it is difficult to prevent scratches on the sides of quartz rods. On the other hand, because sapphire is such a hard material, it is difficult to polish out all the scratches produced on sapphire rods during their manufacture.

YAG is harder than quartz but not quite as hard as sapphire, making it ideally suited for fine side polishing, thereby preventing radiation from scattering from the sides of YAG rods.

When fabricating IC's (which now have device geometries as small as 0.11 microns), it is critical that the IC manufacturing equipment be uniform from tool to tool. Consequently, each component of a semiconductor-fabricating tool must maintain a very high level of uniformity, including a high level of uniformity among light guide rods. YAG provides several unexpected benefits for providing such uniformity, which could not be achieved with sapphire or quartz. These benefits include:

YAG has no birefringence, so it provides more uniform light collection;
  YAG is an isotropic material, so it eliminates problems with growth misalignment and/or machining misalignment that are common to sapphire; and
  YAG can be machined to a tolerance as low as ±0.0001 inches, whereas sapphire can only be machined to a tolerance of ±0.001 inches.

The accuracy of pyrometers can be improved by preventing unintended heat from reaching the detector. When using light guide rods for transmitting radiation from the wafer to the detector, the light guide rod can itself become hot and conduct heat from the process chamber in addition to radiation from the wafer, causing temperature measurement errors. Consequently, the light guide rod should have a low level of thermal conductivity.

Fortunately, YAG has a lower level of thermal conductivity than sapphire. An additional benefit is that lower temperature epoxies can be used for securing ferrules to the YAG rods, and O-rings having lower heat resistance can be used.

The following table provides a summary of the useful properties of YAG.

YAG MATERIAL PROPERTIES

| PROPERTY | YAG |
| --- | --- |
| Crystal Structure | Cubic |
| $Y^{3+}$ Site Symmetry | $D_2$ |
| Lattice Constant | a = 12.013 |
| Standard Orientation | <111> |
| Molecular Weight | 593.7 g mol$^{-1}$ |
| Melting Point | 1965° C. |
| Density | 4.56 g cm$^{-3}$ |
| Thermal Expansion Coefficient | 7.8 × 10$^{-6}$ Å ° C.$^{-1}$ |
| Thermal Conductivity | 13 W m$^{-1}$ K$^{-1}$ |
| Specific Heat ($C_p$) | 0.140 cal g$^{-1}$ ° C.$^{-1}$ |
| MOHS hardness | 8.2 |
| Young's Modulus | 335 GPa |
| Tensile Strength | 2 GPa |
| Thermal Shock Resistance | 8 W cm$^{-1}$ |
| Refractive Index @ 632.8 nm | 1.83 |
| $Y^{3+}$ Site | 1.38 × 10$^{20}$ cm$^{-3}$ |
| $Al^{3+}$ Site (IV) | 1.38 × 10$^{20}$ cm$^{-3}$ |
| $Al^{3+}$ Site (VI) | 0.92 × 10$^{20}$ cm$^{-3}$ |

Another series of improvements for facilitating the measurement of low temperatures is the reduction or elimination of factors causing signal level variations. A number of such factors have been identified, and techniques to improve or eliminate them have been developed as described below.

When using a light guide rod as a radiation collection system, the rod-to-detector coupling efficiency may be reduced by foreign matter that accumulates on the optical faces of the rod and detector. In particular, foreign particles can be deposited on the surfaces when the rod and detector are disconnected. In addition, the mechanical movement associated with connecting and disconnecting the rod deposits debris on the interface surfaces. This debris may adversely affect the measurement system calibration.

FIG. 7 shows a mounting system for prior art light guide rod 84 and detector 88 in which an optical face 92 of light guide rod 84 and an optical face 94 of detector 88 are recessed within a threaded housing 96. This configuration makes cleaning of optical faces 92 and 94 difficult and ineffective.

In contrast, FIG. 8 shows a mounting system of this invention for light guide rod 12 and detector 20 in which optical faces 100 of light guide rod 12 and detector 20 are flush to the edges of their respective housings 102 and 104 and are, therefore, closely coupled. The flush mounting of this invention facilitates easy and effective cleaning of optical faces 100. The close coupling also improves rod-to-detector optical coupling and, thereby, reduces signal transmission variations.

The light guide rods used in this invention typically have minor variations in their ability to capture and propagate radiation, which results in a unique calibration factor for each light guide rod. Temperature measurement errors will result if the calibration data are not properly tracked and entered into the measurement system. Currently the calibration data are entered manually via an external device such as a keypad or PC terminal, rendering the data subject to omissions and/or data entry errors.

FIGS. 9 and 10 show improvements in the measurement system in which each particular light guide rod 12 has an associated electronic calibration key 110 that electronically stores and transmits to the detector 20 and signal processing system 112 signal loss data for the associated light guide rod 12 being used. FIG. 9 shows a freestanding embodiment in which electronic calibration key 110 is tethered by a cable to associated light guide rod 12, and FIG. 10 shows a preferred integral embodiment in which electronic calibration key 110 employs an EEPROM that is integral to a ferrule 116 that captivates light guide rod 12. Electronic calibration key 110 is electrically connected to signal processing system 112 through electrical contacts 118.

When detector 20 and its associated electronics are mounted to a circuit board, output signal variations may result from mechanical stresses caused by circuit board temperature variations or by the circuit board mounting structure. Very small electrical currents are generated by detector 20 when it is measuring low levels of radiation and, consequently, the output signal is subject to variations caused by the associated electronic circuitry. An aspect of this invention is, therefore, structural improvements that minimize the mechanical stresses on the circuit board.

One way of reducing circuit board stress is to mount the electronic components in a mechanically compliant manner, such as by potting the circuit board to the mechanical housing with a silicone rubber potting compound. This efficiently dissipates heat and reduces the effects of circuit board stress.

Another way of reducing circuit board stress is to employ low power dissipation electronic components in the circuit board design.

Referring again to FIG. 1, when taking temperature measurements with radiometric system 10, it is important to block undesirable wavelengths of radiation 14 to reduce errors introduced by heat build-up in filter 18 and detector 20 and to prevent damage to photo detector 20 caused by the undesired wavelengths. Undesired wavelengths of radiation 14 are typically blocked by using filters. Two improved ways of blocking undesired wavelengths are:

When a blocking filter, such as filter 18, performs its function by absorbing radiation, the absorbed energy causes filter 18 to increase in temperature, which changes the blocking characteristics of filter 18, altering the response of the measurement system, and resulting in temperature measurement errors. These errors can be prevented by introducing an additional blocking system for impeding undesirable wavelengths of radiation 14.

A preferred way of accomplishing this additional blocking is to place reflective hot/cold mirror surface 22 coating on filter 18. Hot/cold mirror surface 22 preferably causes minimal change in the spectral characteristics of filter 18 in the desired wavelengths yet transmits wanted wavelengths of radiation 14 while reflecting undesired wavelengths as undesired radiation 120.

Reflecting the undesired radiation 120 back through collection optics 12 (light guide rod or lens) to the location being measured on object 16 is advantageous for the following reasons: the temperature of object 16 is not significantly altered because much of radiation 14 is returned to object 16; and filter 18, photo detector 20, and the associated electronics are more stable because they are not unduly heated by radiation 14.

Figure 11:
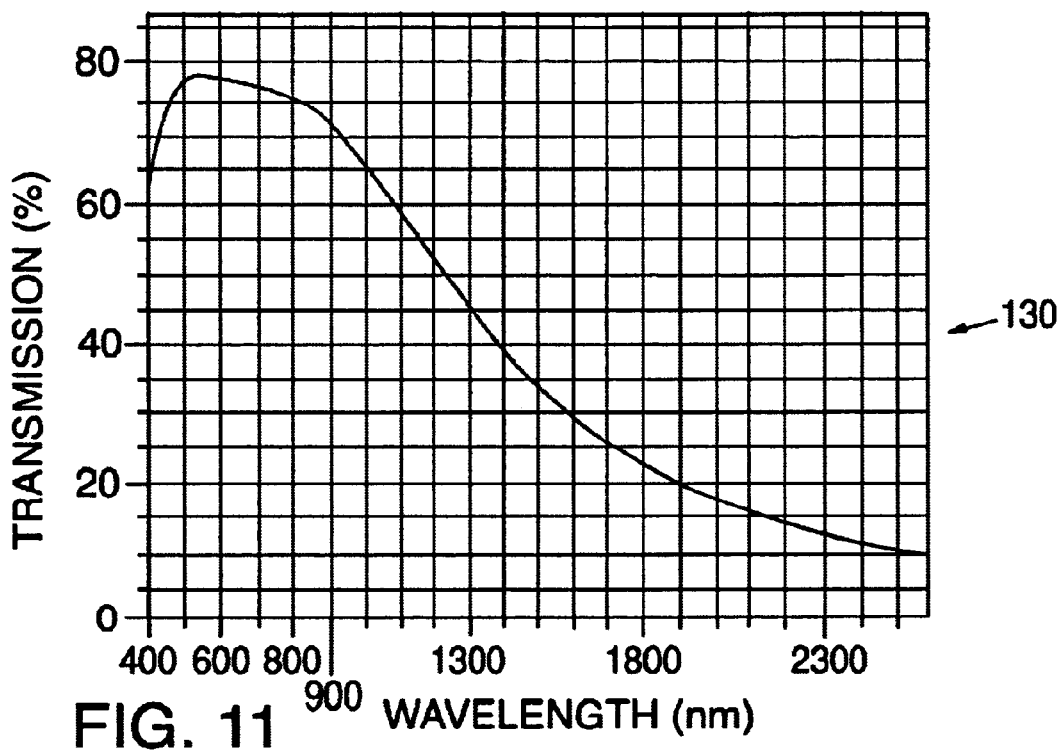
FIG. 11 is a graphical representation of a radiation transmission response as a function of wavelength for a reflective filter of this invention.

FIG. 11 shows a preferred response curve 130 for hot/cold mirror surface 22 of this invention. Hot/cold mirror surface 22 passes at least 70 percent of radiation 14 at about 900 nm and reflects substantial amounts of undesired radiation 120 at wavelengths above about 1,200 nm. Skilled workers will understand that hot/cold mirror surface 22 can be formed from a variety of suitable metallic and dielectric materials.

The response of a detector to radiation 14 and the electrical noise level it generates is a function of its operating temperature. Radiation wavelengths incident on the detector may not produce an electrical signal, but they may alter any existing signal by changing the detector temperature. In particular, short wavelength radiation may permanently alter the response characteristics of the detector. This radiation damage is prevented in part by the above-described hot/cold mirror surface 22 and also by filter 18, which further blocks unwanted radiation wavelengths from the detector. An advantage of the hot/cold mirror is that it prevents UV damage and IR heating, which causes a shift in the wavelength response of the photo detector and also causes electrical noise.

Figure 12:
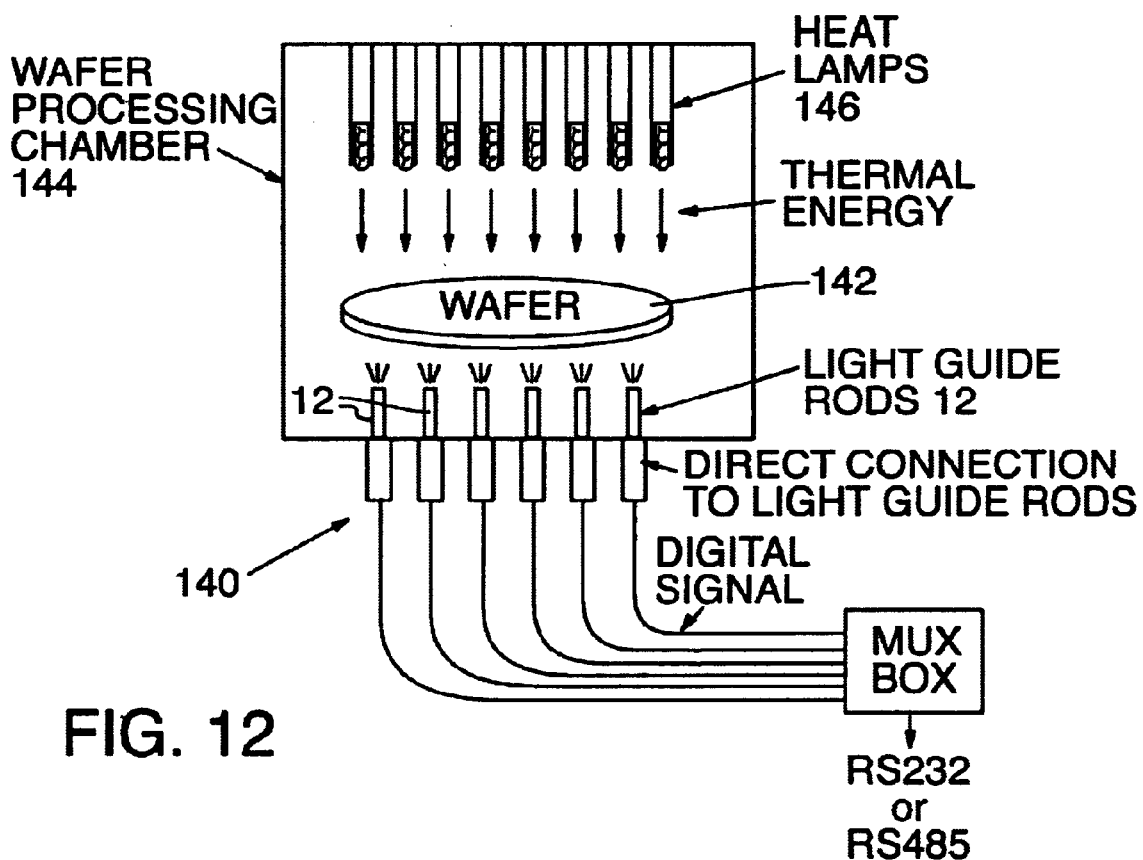
FIG. 12 is a simplified schematic pictorial view of a pyrometer system of this invention employed in a semiconductor process temperature measurement application.

FIG. 12 shows a pyrometer system 140 of this invention employed in a semiconductor processing application. A major application of pyrometer system 140 is measuring the temperature a silicon wafer 142 as it is heated in a processing chamber 144 by high-power lamps 146 or plasma (not shown). Lamps 146 are typically mounted on the opposite side of silicon wafer 142 from light collection optics 12.

Figure 13:
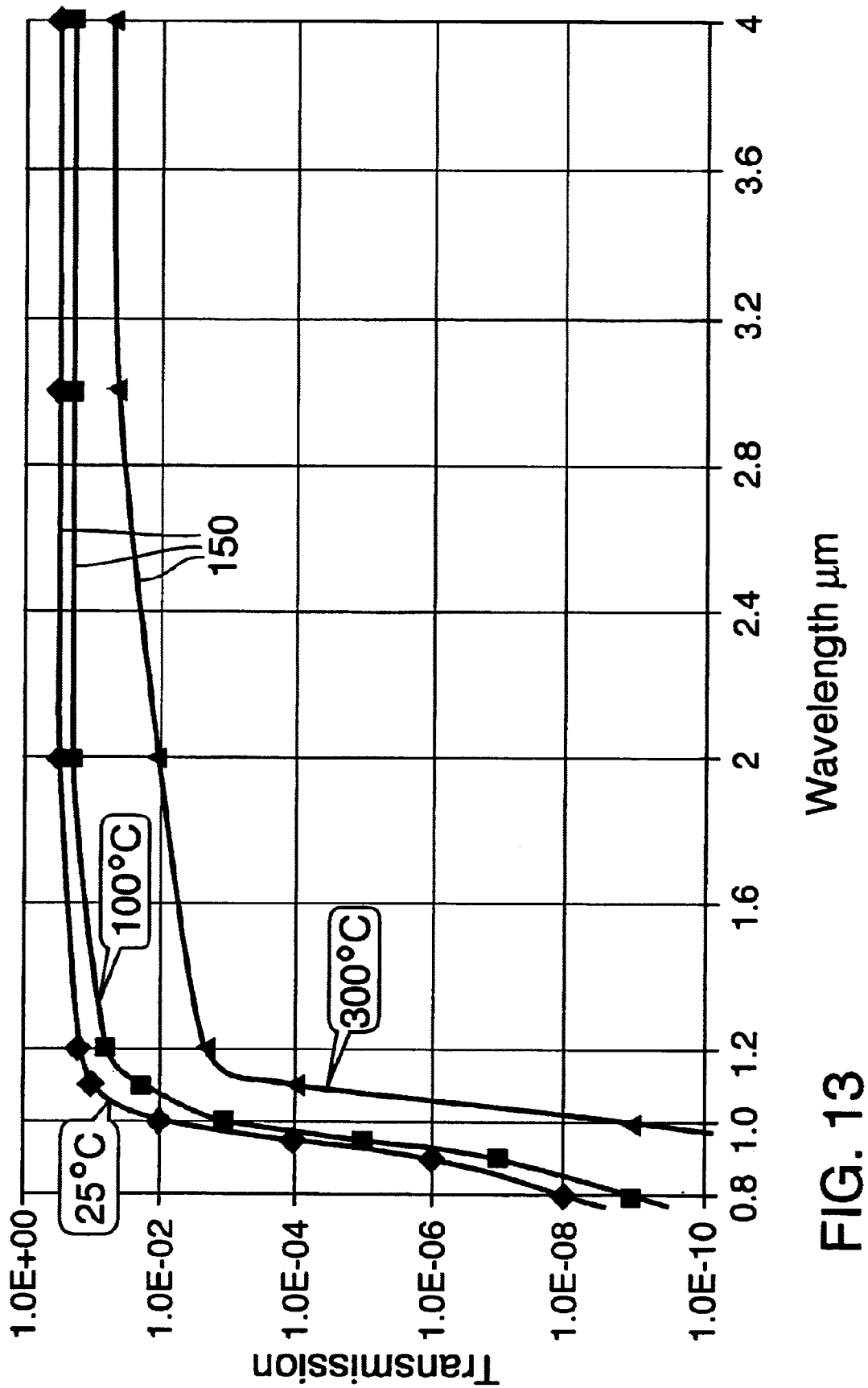
FIG. 13 are graphs representing the transmission of radiation through a silicon wafer as a function of wavelength and temperature.

FIG. 13, shows graphs 150 representing the transmission of radiation through a silicon wafer as a function of wavelength and temperature. Graph 150 shows that silicon wafer 142 is transparent to radiation beyond a wavelength of about 1,000 nm. Therefore, it is important to block radiation beyond 1,000 nm to prevent detector and filter heating that would cause temperature measurement errors. Several wavelength blocking techniques are aspects of this invention.

A common technique for achieving wavelength blocking is employing a short wavelength pass filter, which is fabricated by vacuum evaporation of optical materials having varying indices of refraction. By stacking a series of such materials, typically alternating high and low indices or refraction, a coating is produced that reflects or absorbs radiation over a limited range of wavelengths. To achieve blocking over a broad range of wavelengths, it is necessary to place successive stacks on top of each other such that each stack blocks a different wavelength range.

Figure 14A:
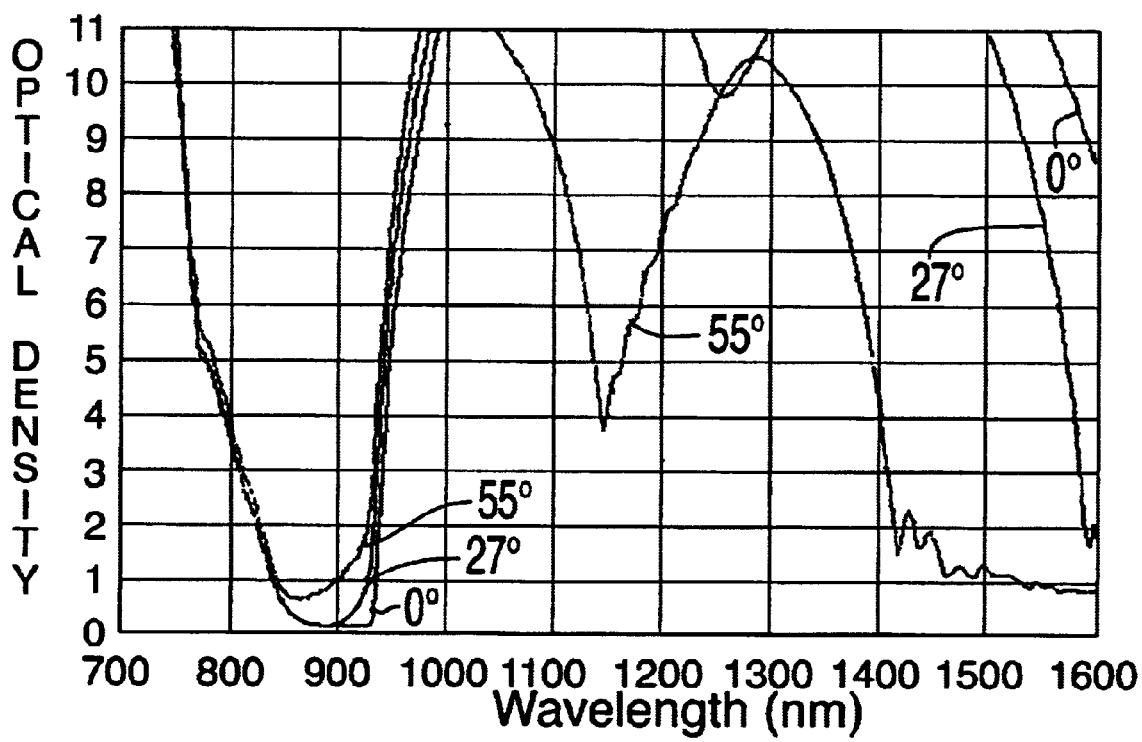
FIGS. 14A and 14B is graphs representing respectively the optical density and transmittance as a function of wavelength and radiation incidence angles of a short wavelength pass filter of this invention.
Figure 14B:
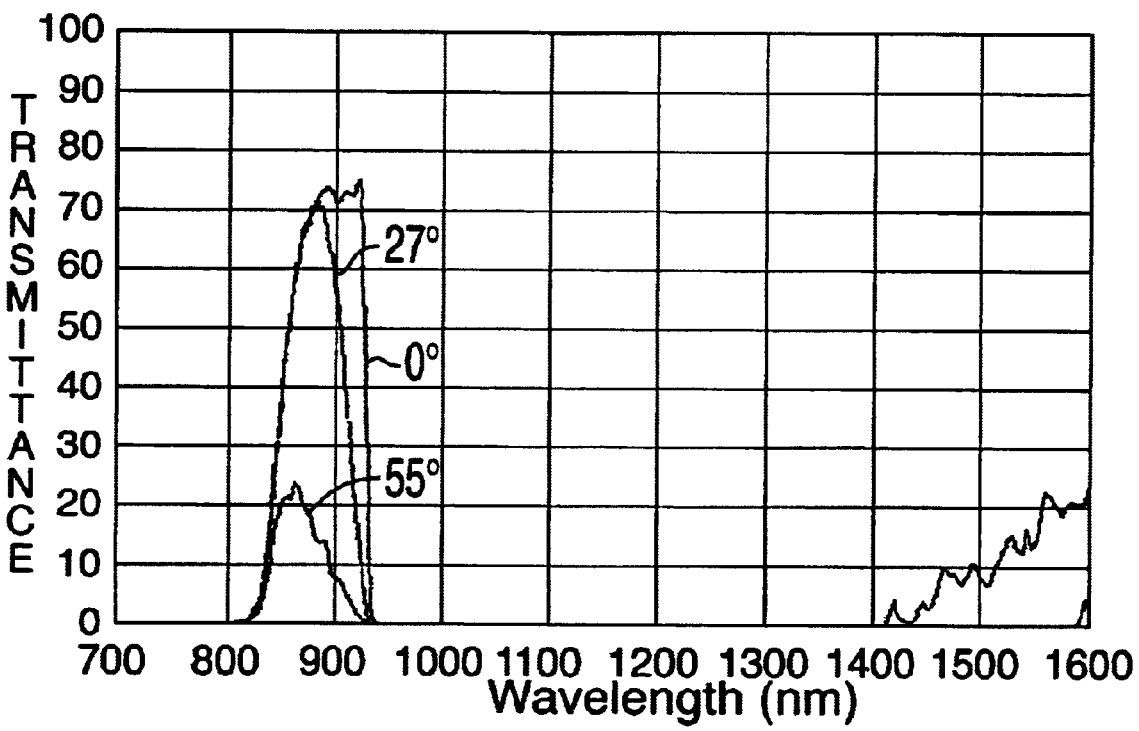

FIGS. 14A and 14B represent the respective optical density and transmittance versus wavelength and radiation incidence angle of a short wavelength pass filter that us suitable for use in this invention. Skilled workers will understand how to make such a filter. As shown in the graphs, this technique is most effective if the radiation is incident to the filter over a range of angles less than about 27 degrees. However, if the radiation is incident over a wide range of angles, e.g., up to about 55 degrees, the wavelength blocking characteristics are altered.

A suitable short wavelength pass filter, therefore, includes a blocking coating that includes as a design parameter the numerical aperture of the light guide rod or optical fiber that propagates the light from the sample to the detector.

Another embodiment of this invention employs gallium aluminum arsenide ("GaAlAs") and other wavelength-selective detector materials in place of band pass filters.

Figure 15:
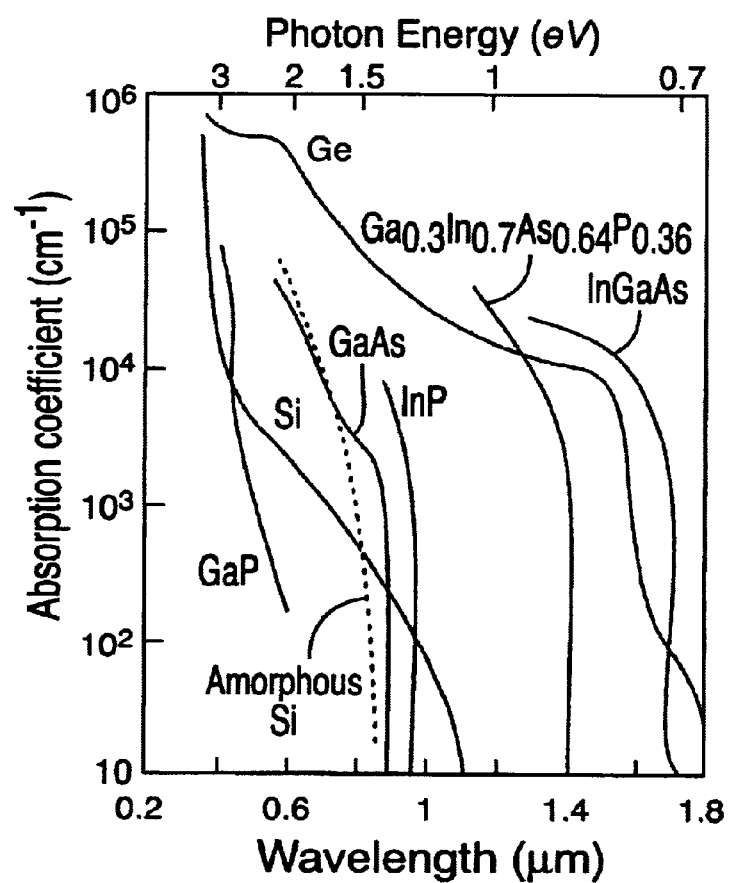
FIG. 15 is a graph representing the absorption coefficient of various detector materials as a function of wavelength.
Figure 16:
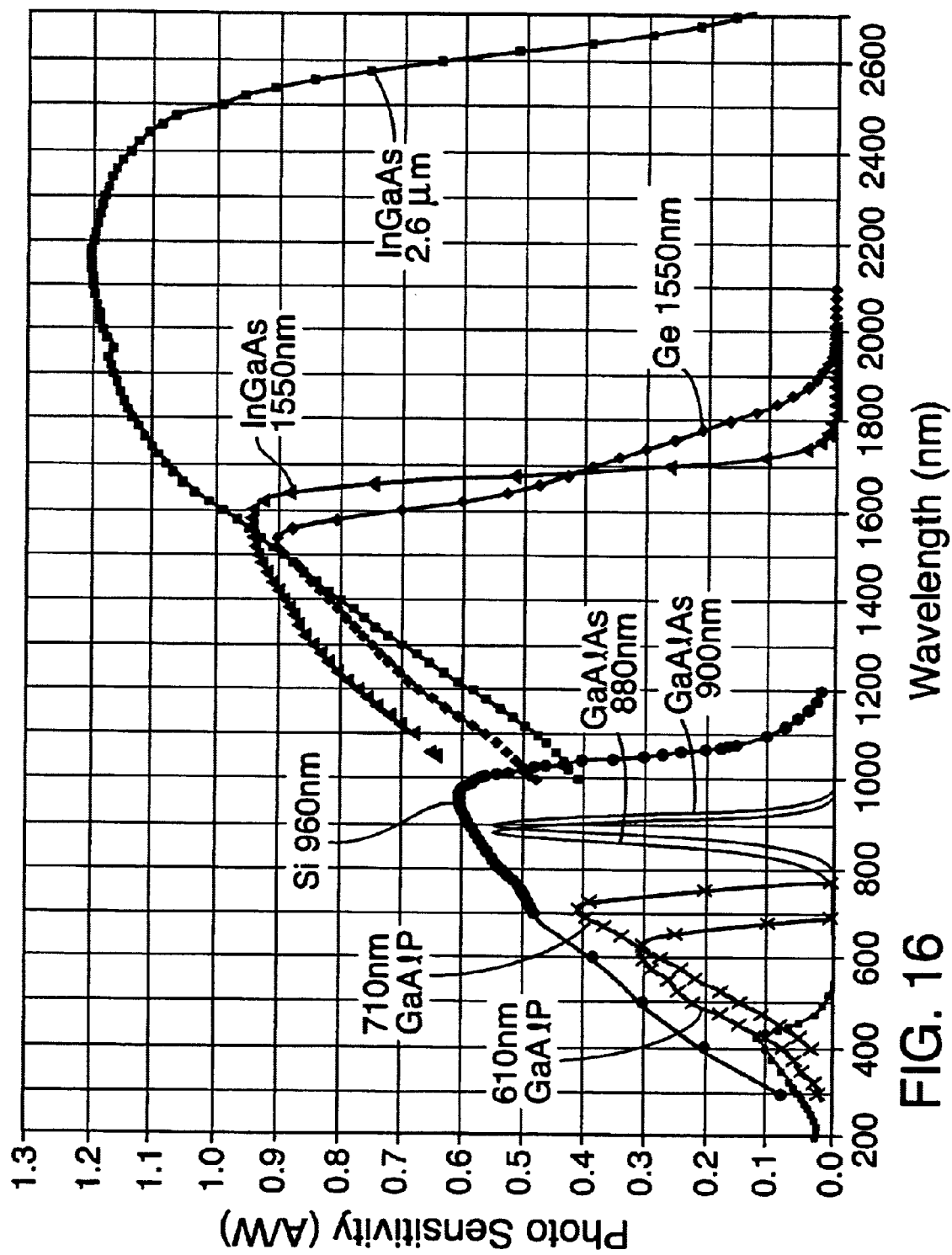
FIG. 16 is a graph representing the photo sensitivity of various detector materials as a function of wavelength.

FIGS. 15 and 16 represent the respective absorption coefficient and photo sensitivity of various detector materials as a function of wavelength. Conventional pyrometer detectors utilize either InGaAs or silicon detectors. InGaAs detectors are sensitive to radiation wavelengths as long as 2,700 nm, which makes blocking very difficult. Silicon detectors are nominally insensitive to wavelengths longer than 1,200 nm, however the photo sensitivity of silicon diminishes with longer wavelengths.

An aspect of this invention, therefore, is to utilize a detector material having a photo sensitivity that diminishes rapidly at wavelengths at which silicon wafers begin to transmit radiation. A preferred detector material is GaAlAs, which has a photo sensitivity peak at 900 nm and diminishes by about three orders of magnitude at 1,000 nm. Alternatively, detectors materials such as GaP, GaAsP, GaAs, and InP are suitable for use as wavelength-selective detectors at wavelengths less than 1,000 nm.

The photo detector materials for wafer temperature measurements are chosen for photo sensitivity around the optimum wavelengths for measuring silicon, GaAs, and InP wafers. In particular, the material is chosen for sensitivity at wavelengths shorter than the 1,000 nm (bandgap for silicon wafers), yet as long as possible to provide a maximum amount of Planck Blackbody Emission without significant sensitivity to radiation transmitted through the wafer.

The preferred photo detector is made from GaAlAs, a tertiary compound, and is doped to optimize its photo sensitivity around 900 nm. This detector material is advantageous because it is insensitive to radiation wavelengths transmitted through a silicon wafer, and to much visible ambient light. It is also advantageous because it has a narrow wavelength detection sensitivity, minimizing the need for an additional wavelength selective filter. A suitable detector is manufactured by Opto Diode Corporation, located in Newbury Park, Calif.

Of course, in situations where sharper cutoff is desired, the detector can be combined with a filter to achieve a wavelength selectivity compounding affect. In these situations, it is also easier to design and manufacture band pass filters that are matched for use with the particular detector material.

The ability to eliminate the filter altogether (along with the ability to use a simple band-pass filter when one is required) further allows the detector to be spaced much closer (0.25 mm verses 2.54 mm) to the light pipe, enabling collecting about ten times more radiation. The close spacing also provides better low temperature measurement performance, e.g., the ability to measure 200° C. compared to 350° C. with a traditional band-pass filter and a silicon broad band detector.

Figure 17:
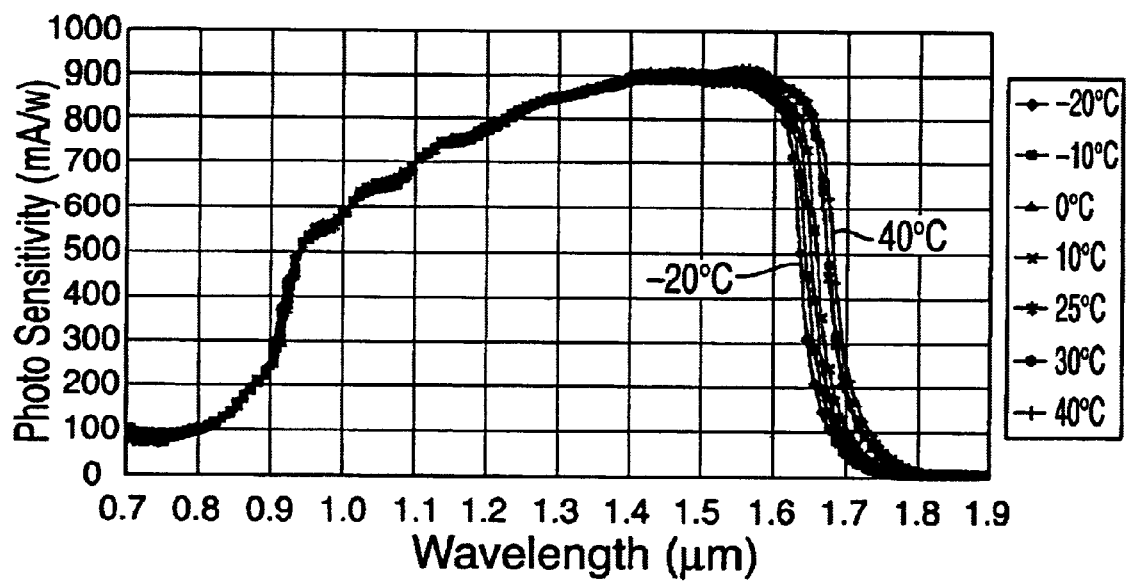
FIG. 17 is a graph representing photo sensitivity versus wavelength as a function of photo detector temperature.

As shown in FIG. 17, detector photo sensitivity changes with temperature, which causes output current variations that correspond to temperature measurement errors. Prior methods for dealing with this problem are to: 1) not correct for the error and simply specify a lower accuracy/repeatability specification; 2) use a band pass or cutoff filter to attenuate the detector wavelength selectivity skirts, thereby eliminating most of the spectral shifting variations; and 3) calibrate out errors by taking a set of measurements at various ambient and target temperatures and use the resulting data to extrapolate correction data.

Method 1 is clearly unacceptable for precision measurements.

Method 2 works well, although there are some remaining fluctuations caused by spectral shifts in the filter and detector. This method also significantly reduces the ability to measure lower temperatures because infrared wavelengths of interest are attenuated by the filter.

Method 3 also works well but is limited to the calibrated range of temperatures and is only relevant to systems of a similar configuration. The accuracy of this method is also limited by the conditions under which the data are taken and diminishes with higher target temperatures because of the difficulty of making accurate blackbody furnace measurements at these temperatures. In addition, this method is time consuming, limited in flexibility, and is not based on first principles of physics, making it prone to inaccuracies.

An improved method is to employ correction data generated from detector photo sensitivity curves as a function of wavelength, such as the curves shown in FIG. 17. A detector that is representative of the detectors used in a particular instrument model, is characterized with a monochromator at various ambient temperatures, such as 0, 10, 20, . . . 60 C., to generate a set of data. The data are then used to generate scale factor correction data for detector current vs. temperature using the Planck equation and integrating the area under the spectrum curve vs. target temperature.

The data entered into the software are ambient dependent detector spectrum curves, minimum theoretical target temperature, maximum theoretical target temperature, and one actual predetermined target temperature.

Figure 18:
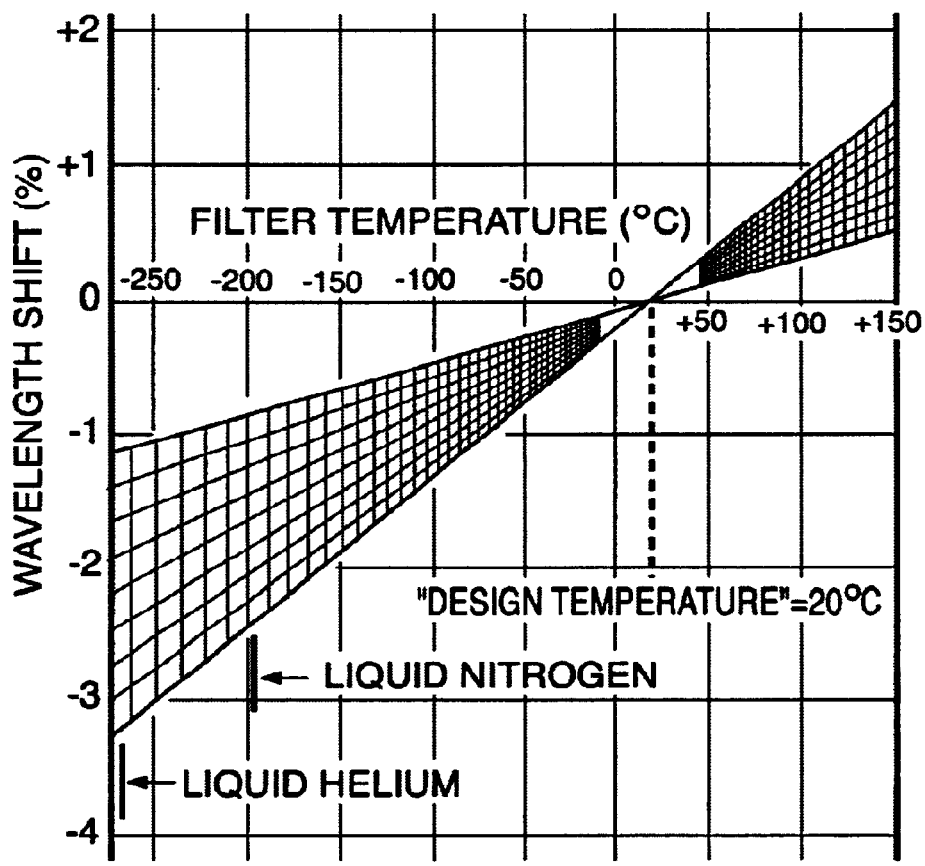
FIG. 18 is a set of graphs representing wavelength shift as a function of temperature for typical infrared interference filters.

This same correction method can be used for correcting for other optical components, such as optical filters that vary with ambient temperature. FIG. 18 shows a set of graphical data representing wavelength shift as a function of temperature for typical infrared interference filters. Suitable correction data can be extracted from such data.

Yet another series of improvements for facilitating the measurement of low temperatures are embodied in the software controlling the signal processing of this invention. Several improvements are set forth below.

Controlling integration timing: The electrical signal generated by the detector is extremely small and care must be taken to avoid introducing extraneous noise into the detector that would degrade the measurement accuracy. A common technique for signal processing is to integrate the charge from a detector for a period of time and use the accumulated charge as a measure of signal level. Errors result if the integration time varies. Three methods of controlling integration time are described below.

Integrating ADCs are devices that sample a physical phenomenon by exposing a circuit element to the phenomenon for a precise time interval referred to as an "integration interval." In practice, a microprocessor generates this interval. This can be done directly by the microprocessor or with external hardware. External hardware takes valuable physical space, requires additional operating power, generates unwanted heat, and is generally less programmable than a microprocessor. On the other hand, direct microprocessor control has not been previously possible because of instruction timing irregularities, limits on instruction rate, interrupt latencies, or a combination of these problems.

Three methods presented below can be used to overcome the above-described microprocessor limitations and provide direct, precise integration period control.

Interrupt Jitter Control: An interrupt is an asynchronous redirection of program logic based on some event. In this context, an interrupt would be based on an internal timer in the microprocessor. Most microprocessors have such a timer, typically consisting of a clock input (usually the processor clock divided by some integer prescaler) and a counter. The counter is loaded with some initial value and then counts up or down until it reaches a predetermined limit. When the limit is reached, a processor interrupt is issued for redirecting execution to an interrupt service routine ("ISR"). Interrupt jitter refers to a variable delay that is introduced by the processor between the time the interrupt is issued and the time when the ISR is actually entered. This time delay is caused by some instructions taking longer than others to execute, and the current instruction always completing before the interrupt is recognized. On some processors, an instruction pipeline can introduce additional delays. In an integrating ADC application, the ISR is responsible for generating the integration period, thus error is introduced by interrupt jitter.

One method of controlling interrupt jitter is to ensure that the processor is always in the same state when an interrupt occurs. The main program occasionally reads the interrupt timer counter, and when it is near expiration, drops into a series of identical, harmless instructions (no-ops work well). A sufficient number of no-ops instructions are placed in series so that when the counter is nearly expired, it is predictable that the interrupt will occur during the no-ops, thus the processor will always be executing the same instruction when the interrupt occurs.

This method has high processor overhead because the main program must accommodate the timer monitoring, and processing time is wasted in the no-op section. Also, processor intervention is required for every integration line edge which is generated. Consequently, while this method allows the microprocessor to control the "integration interval", it is an undesirable methodology because it consumes excessive processing capacity, leaving insufficient capacity to perform other required functions.

Capture-Compare Unit: Some processors contain a Capture-Compare Unit ("CCU") that can be used to control the integration period. The CCU consists of a counter running at high speed, and a compare register for comparing against the counter value. When the counter value equals the compare register value, an output is toggled to generate the integration period, and an interrupt can be generated. The purpose of the interrupt is to cause an ISR to reload the counter with the next required value for the next integration period. This interrupt may jitter without harm, because the CCU hardware has already toggled the output controlling the integration time.

This method works, but there is a lower limit on the integration times that can be generated because the processor must recognize the interrupt and execute enough instructions to reload the compare register before the counter has advanced too far. This method has medium processor overhead, because every integration line edge requires processor intervention. Consequently, while this method allows the microprocessor to control the integration interval, it is not a preferred methodology.

Synchronous Serial Port Control: This is the preferred method of this invention. Most processors contain a synchronous serial port ("SSP"). An SSP can generate a high-speed clock and send data, one bit at a time, on each clock edge. SSPs are widely used to propagate data between CODECs and digital signal processors.

To use an SSP for controlling integration times, the SSP is configured to generate a high-frequency clock. The frequency of the clock determines the timing resolution of the integration interval. The processor then generates a stream of words through the SSP, and the SSP data output controls the integration timing. Usually an SSP will accept 16- or 32-bit words of data at a time, and for the next 16- or 32-bit periods, sends that word one bit at a time. SSPs generate an interrupt when a word is complete, and are generally double-buffered, meaning that one word can be shifted out while another one is loaded by the microprocessor.

In the pyrometry application of this invention, the processor is only required to load a new word every 16- or 32-clock periods, and when the interrupt occurs, there is a full word-time to respond and reload the SSP with the next word. This method is advantageous because it has the lowest processor overhead, it overcomes interrupt jitter, requires no special main program structure, and can generate arbitrarily high-resolution integration times.

Improving integration measurements: An integrating ADC samples a signal by exposing a storage capacitor to the signal for a precise time period, and then measuring the charge on the capacitor to determine the magnitude of the input signal. To increase the dynamic range of an integrating ADC, there are usually several "ranges" available, each employing a different value storage capacitor, thereby enabling the ADC to measure lower or higher input signals by choosing a smaller or larger capacitor. The output of the ADC is a number ranging from zero to n−1, where $n=2^{number\ of\ ADC\ bits}$. Therefore, a 16-bit ADC will produce values from zero to 65,535. The center of this range is 32,768.

Range Centering for Integrating ADCs: Auto-Ranging is a process of automatically choosing a range that accommodates the present input value. The challenge of any auto-ranging scheme is to accurately track changes in input signal such that the input signal never exceeds the measurement capability of the ADC's range. While perfect auto-ranging is not possible, (see note below) an aspect of this invention provides an auto-ranging technique that allows the input signal to swing the maximum amount up or down within an integration cycle without exceeding the measurement capabilities of the ADC.

One auto-ranging method is range centering in which the controlling software dynamically adjusts the integration time to maintain the ADC output in the center of its range. For example, if a 16-bit ADC is used, the software tries to keep its output at 32,768 by adjusting the integration time and the range capacitor. Using this control method is advantageous because it integrates for a time that allows the input signal to swing the maximum amount up or down within an integration cycle without exceeding the measurement capabilities of the ADC.

Note: In a system with arbitrary input signals, perfect auto-ranging is not possible, because rapid input variations can occur within integration periods. If an integration is taken from time t to t+1 Second, but a step input change occurs at time t+0.01 Second, the ADC may not be in an appropriate range to measure the new input value. Furthermore, the controlling software will not recognize this until at least t+1 second, at which time the ADC value may be saturated at its maximum or minimum value. Step inputs are not common, however, because most measurement systems measure physical quantities related to matter that does not change state instantly or even very rapidly.

A Method of Decreasing Auto-Range Response Time: When input signals are small, long integration times must be used to develop measurable charge on the integrating capacitor. As described above, this can cause the current range to be exceeded by the input signal if the signal changes rapidly. One way to improve the auto-range response time is to use a shorter integration period for every other measurement. For example, the first integration period might be set to 0.1 second, and the next to 1 second. The conversion for the first integration period is available a short time into the second integration period. Since the first integration period is shorter, it can handle more input signal without saturating. Furthermore, since this conversion is available a short time after the longer integration starts, the controller has an opportunity to cut the longer integration short, thus avoiding saturation and improving transient response. For example, if the first integration is set to 0.1 second, and the next integration is set to 1 second, and the maximum value of a sampling conversion is 1,000, then the controller can know that if the short (0.1 second) integration yields a value of over 100, then the longer integration is going to overflow. It can use this information to shorten the longer integration and prevent it from ever becoming saturated. This method improves the response time of an initial signal upward slope, which occurs frequently in pyrometry as an object is initially heated.

Range Flooring for Integrating ADCs: When the input signal is rapidly decreasing, it can fall below the acceptable minimum for the present range of the ADC. When this happens, the ADC may return an erroneously small value. A lower range needs to be quickly selected without dropping the erroneous readings, thereby causing a spike in the data.

One such method is to "floor" the value, rather than drop the bad value or allow it to produce a large spike in the output data. "Flooring" is the process of replacing readings below a certain value (or floor) with the floor value. A floor value can be chosen globally or per-range. This ensures that when the ADC measures small input signals relative to its current range, reasonable output values are still produced.

Variable-Depth Averaging for Variable-Speed Sampled Systems: Sampled systems take instantaneous readings (samples) of a physical quantity at successive points in time. If the intervals between samples are constant, the system is a fixed-speed sampled system. If the intervals between samples change based on the measured quantity or some other system parameter, the system is a variable-speed sampled system. The sampling speed is defined as f.

Noise in a sampled system is an undesirable secondary signal which appears along with the quantity to be measured. It can be introduced from the detector, the connections to it, or the components of the measurement circuit. To read a sensitive transducer, noise reduction techniques should be employed.

The simplest form of noise reduction is to take the average of a certain number of samples, looking back in time from the current sample. If the number of samples to be averaged is defined as n, then n samples must be stored in a buffer. As each new sample is taken, the oldest sample is dropped from the buffer, the new sample is stored in the buffer, and a new average is taken. The buffer is deep enough such that both high and low values of the noise signal will be present, and averaging this random signal will reduce it significantly. The averaged samples are called the "output samples" to differentiate them from the raw samples which feed the average buffer.

Problems: In a variable-speed sampled system, the changing sampling rate causes a sample buffer to represent differing amounts of time. With a sample buffer size of 100, a sample rate of 1 Hz represents 100 seconds of data. The same buffer at 500 Hz represents only 0.2 seconds. This changes the filter transfer characteristics of the buffer. For example, if there is low-frequency noise present in the signal, the 0.2 second buffer might not contain enough data to filter out the noise. Response time is another problem. At a 1 Hz sample rate, if the signal rises rapidly the effect is delayed by many seconds in the output samples.

Variable-Depth Averaging: To overcome these problems, a variable-depth averaging scheme can be employed in which the output sample rate is fixed, and is represented by the variable o. The depth of the average buffer (n) changes with the input sample rate, and is calculated as a ratio of o, f, and a third variable k, which is a depth factor that may be constant or change with the input sample rate, and represents the number of output sample periods represented in the buffer. Variable k is greater than 0, but may be greater or less than 1. The depth calculation is:

$$n=kf/o$$

For example, if the output sample rate is 1 Hz, the input sample rate is 1 Hz, and k is 1, then no averaging would occur because the buffer depth is 1*1/1. If the input sample rate increases to 10 Hz, the buffer depth is 1*10/1, or 10 samples.

When the input sample rate is faster, the average buffer becomes larger. For very fast rates, it may be undesirable to have so many samples averaged due to transient response times of a large average buffer. For such rates, k may be chosen to be fractional, thus shrinking the average buffer. For low input sample rates, it may be desirable to choose a larger k value to provide better noise suppression.

Changing Buffer Depth: When buffer depth is changed, care must be taken to suppress transients in the output samples. There are two cases to consider; growing and shrinking the buffer.

Shrinking: If the system has been averaging 100 samples to generate an output sample, and the input changes such that a new depth of 10 samples is used, then using only the last 10 samples may cause an output sample "spike" to occur. Two techniques can be used to suppress this spike. The first is to take 10 evenly-spaced samples from the 100 points in the old buffer and use these to fill the new smaller buffer. The second is to gradually shrink the buffer over many input periods.

Growing: When the buffer is to be expanded, the old smaller buffer is copied into the new larger buffer, and new samples are put into the buffer until it becomes full. In the interim, output samples are generated based on the number of points in the buffer, not the buffer size. This causes no transients on the output, but may cause more dampened responses to input transients. This is expected with a greater averaging depth.

Using variable-depth averaging to sample a signal and filter out undesirable noise and employing techniques for growing and shrinking buffer sizes are aspects of this invention.

Field of view compensation: The ability to read temperatures at or below room temperature using short wavelengths is a novel and unique circumstance, as heretofore the pyrometers were only able to read source temperatures which were significantly higher than room temperature and therefore higher than the temperature of the pyrometer. When measuring the temperature of an object that is at or below room temperature using short wavelengths, the temperature of the collection device may now be equal to or higher than that of the desired source. When this occurs, the detector will sense the energy emanating from proximate objects such as the lens and housing instead of or in addition to that emanating from the desired target source. An improvement therefore is to design the detector and its surrounding housing such that it can distinguish between the temperature of the source and the temperature of its surrounding objects in order to obtain a reading of the desired source.

Reflective field-of-view housing: One method for the detector to distinguish between the temperature of proximate objects and the target source is to design the instrument housing such that it becomes invisible to the detector. This can be accomplished by designing the lens assembly and detector housing such that all surfaces of non-target objects in the FOV of the detector are reflective or coated with a reflective material such that they become invisible to the detector.

Compensating for temperature of optical housing parts in the FOV: One such method for preventing the temperature of proximate objects from influencing the signal measurement of the target source is to measure and track the temperature of all non-target objects in the FOV of the detector and then take them into consideration in the calibration procedure. This can be accomplished by installing temperature sensors next to the objects in the detector's FOV to monitor their temperatures and to then feed the information as a variable in the calibration calculations.

Detector signal compensation: When using short wavelength detectors such as the InGaAs detector and the signal of the target heat source (source signal) is within a factor of 10 or less of the signal generated by the detector (detector signal), the detector signal becomes strong enough to cause errors in source temperature readings and must be taken into consideration and corrected for when taking a low temperature reading. Heretofore this had not been a problem since the target heat source was always at higher temperatures and its signal overwhelmed the signal of the detector to such a degree that the detector signal was not a factor in the measurement. In addition, as the source signal became weaker with the lowering of the source temperature, the noise of the amplifying electronics became controlling as it then overwhelmed the source signal before the detector signal became a factor in the reading. The amplifying electronics noise was the limiting factor in determining how small a source signal could be read.

With the significant reduction in amplifying electronics noise brought about by this invention, source signals can now be read down at levels where detector's self generated signal becomes a factor, thus requiring a new calibration technique to adjust for the detector signal. It is an aspect of this invention to provide individual techniques and a combination of techniques for compensating for the detector signal when calibrating an instrument that is reading source signals within a factor of 10 of the detector signal. It should be noted that it is possible to reduce the detector/electronics signal so that the heat source may also be brought lower.

One method for doing this is to cool the detector, either physically (externally) or electronically (internally). While this enables a lower source signal, the detector signal will eventually come into play.

Another calibration technique is to point the instrument at a calibrated target whose temperature is both known and at a low enough temperature for the detector signal to be readable. Once the detector signal is read, the target temperature is changed a known amount and the subsequent corresponding change in detector signal error can then be observed. Once the detector signal error becomes known, it can be measured and compensated for in the calibration procedure (which involves cycling the instrument through various ambient temperatures and correcting for variances). Compensating for the detector's self generated signal by changing a known calibrated target source a known amount is also a specific feature of this invention.

Regarding pyrometer calibration, zero offset is defined as the lowest signal level indicated by the pyrometer system. This signal level is below the minimum change in target temperature the pyrometer can resolve. The zero offset level can be determined by using a high emissivity (E>0.80) target at a fixed low temperature that occupies the full FOV of the pyrometer. This works for a pyrometer having a measurement wavelength in a region of the blackbody emission curve whose amplitude is increasing with increasing wavelength (less than ~2,600 nm.) and may have a cooled or an uncooled detector. A reflective entity that occupies the full FOV of the pyrometer for purposes of generating a true zero offset, meets the above conditions.

Skilled workers will recognize that portions of this invention may be implemented differently from the implementations described above for preferred embodiments. For example, the description above applies primarily to temperature measurements of target media, but also applies to various forms of light measurements.

It will be obvious that many changes may be made to the details of the above-described embodiments of this invention without departing from the underlying principles thereof. Accordingly, it will be appreciated that this invention is also applicable to temperature measurement applications other than those found in semiconductor processing. The scope of this invention should, therefore, be determined only by the following claims.

We claim:

1. A radiometric temperature measurement system that performs a measurement of a temperature of a target medium, comprising:
   a light guide formed of a material including yttrium aluminum garnet (YAG), the light guide configured for collection of radiation emitted by the target medium, the radiation collected having an intensity and occupying a range of wavelengths representing the temperature of the target medium;
   a radiation detector receiving the radiation collected by the light guide to provide a signal that is indicative of the temperature of the target medium; and
   an electronic circuit that processes the signal to provide the temperature measurement, the electronic circuit including an analog-to-digital converter (ADC) with an auto-ranging capability that adjusts an integration time of the ADC to maintain an output that is substantially centered between a minimum value and a maximum value.

2. The measurement system of claim 1, in which the target medium is a semiconductor wafer undergoing a chemical vapor deposition (CVD) process.

3. The measurement system of claim 1, in which the target medium is a semiconductor wafer undergoing a physical vapor deposition (PVD) process.

4. The measurement system of claim 1, in which the target medium is a semiconductor wafer undergoing rapid thermal processing (RTP).

5. The measurement system of claim 1, in which the target medium is a semiconductor wafer undergoing a plasma assisted chemical vapor deposition process or a plasma assisted etching process.

6. The measurement system of claim 1, in which the target medium is a semiconductor wafer undergoing a epitaxy process.

7. The measurement system of claim 1, in which the target medium is a semiconductor wafer undergoing a chemical mechanical polishing (CMP) process.

8. A radiometric temperature measurement system that performs with low temperature measurement sensitivity noncontacting measurement of a temperature of a target medium, comprising:
   a radiation emission collector including a probe element configured for noncontacting collection of radiation emitted by the target medium, the radiation collected by the probe element having an intensity and occupying a range of wavelengths representing the temperature of the target medium;
   a radiation detector receiving a portion of the radiation collected by the probe element, the radiation emission collector directly coupled to the radiation detector to provide to it low loss transmission of the portion of the radiation collected, the radiation detector having a narrowband wavelength selective spectral response characteristic that enables the radiation detector in response to wavelengths of radiation within the range of wavelengths to provide a signal that is indicative of the temperature of the target medium; and
   an integrating converter that is responsive to the signal provided by the radiation detector, the signal having a signal amplitude that is indicative of the temperature of the target medium, and the integrating converter providing after each of successive integration intervals a sample output signal corresponding to the signal amplitude, the successive integration intervals occurring in a timing sequence in the absence of timing jitter caused by interruption of any one of the successive integration intervals.

9. The measurement system of claim 8, in which the radiation emission collector further comprises an optical filter tuned to reject wavelengths of radiation not within the range of wavelengths representing the temperature of the target medium.

10. The measurement system of claim 8, in which the target medium includes a semiconductor wafer and the low temperature measurement sensitivity includes temperatures less than about 35° C.

11. The measurement system of claim 8, in which the probe element comprises a light guide formed of aluminum oxide crystals.

12. The measurement system of claim 11, in which the light guide formed of aluminum oxide crystals is of a yttrium aluminum garnet (YAG) type.

13. The measurement system of claim 11, in which the light guide formed of aluminum oxide crystals is of a yttrium aluminum perovskite (YAP) type.

14. The measurement system of claim 8, in which the radiation detector comprises a solid-state detector material including gallium aluminum arsenide (GaAlAs).

15. The measurement system of claim 14, in which the spectral response characteristic is of a bandpass type and has a radiation responsivity that peaks at about 900 nm and diminishes by about three orders of magnitude at 1,000 nm.

16. The measurement system of claim 8, further comprising a hot/cold mirror positioned between the probe element and the radiation detector, the hot/cold mirror reflecting back to the specimen radiation that is collected by the probe element and is of wavelengths not within the range of wavelengths, the radiation reflected back to the target medium contributing to a maintaining of the temperature of the target medium.

17. The measurement system of claim 16, in which the reflected radiation propagates through the probe element to the target medium.

18. The measurement system of claim 8, in which the integrating converter comprises a microprocessor having a synchronous serial port (SSP) that is capable of generating a high-speed clock having high-speed clock periods and sending data serially in response to occurrences of clock edges, the SSP being configured to provide the timing sequence of successive integration intervals by accepting a number of bits forming a word representing an integration interval and delivering an output signal representing the word, the output signal being delivered serially without interruption during a number of the high-speed clock periods equal to the number of bits, thereby eliminating timing jitter by preventing an interruption before completion of any one of the integration intervals.

19. The measurement system of claim 8, in which the integrating converter is configured to operate with multiple signal value ranges, each of which is associated with multiple integrating storage devices, and has an auto-ranging capability to select automatically a signal value range that can accommodate a present value of an input signal, the integrating converter having successive integration intervals of alternating shorter and longer lengths to decrease an auto-ranging response time of the integrating converter to the signal amplitude when it is rapidly increasing.

20. The measurement system of claim 8, in which the integrating converter is configured to operate with multiple signal value ranges, each of which is associated with multiple integrating storage devices, and has an auto-ranging capability to select automatically a signal value range that can accommodate a present value of an input signal, the integrating converter having for each of the signal value ranges a floor value below which the sample output signal produced by the integrating converter cannot drop, irrespective of the signal amplitude, thereby to prevent production of an erroneous sample output signal whenever the signal amplitude decreases rapidly.

21. The measurement system of claim 20, in which the floor value is different for each of the signal value ranges.

22. A radiometric temperature measurement system that performs with low temperature measurement sensitivity noncontacting measurement of a temperature of a target medium, comprising:
a radiation emission collector including a probe element configured for noncontacting collection of radiation emitted by the target medium, the radiation collected by the probe element having an intensity and occupying a range of wavelengths representing the temperature of the target medium;
a radiation detector receiving a portion of the radiation collected by the probe element, the radiation emission collector directly coupled to the radiation detector to provide to it low loss transmission of the portion of the radiation collected, the radiation detector having a narrowband wavelength selective spectral response characteristic that enables the radiation detector in response to wavelengths of radiation within the range of wavelengths to provide a signal that is indicative of the temperature of the target medium; and
an electronic circuit that processes the signal to provide a temperature measurement, the electronic circuit including an analog-to-digital converter (ADC) with an auto-ranging capability that adjusts an integration time of the ADC to maintain an output that is substantially centered between a minimum value and a maximum value.

23. The measurement system of claim 22, in which:
the electronic circuit further comprises at least one temperature sensor to monitor a temperature of at least one temperature-sensitive component; and
the electronic circuit corrects the temperature measurement based on information obtained from the temperature sensor.

24. The measurement system of claim 23, in which at least one temperature sensor monitors a field of view of the radiation detector.

25. The measurement system of claim 23, further comprising a housing and a printed circuit board, and in which the electronic circuit includes the printed circuit board and is confined within the housing by a flexible, thermally conductive potting compound.

26. The measurement system of claim 22, in which the ADC operates with a variable sampling frequency and is associated with a variable depth buffer for averaging a variable number of samples.

27. A radiometric temperature measurement system that performs with low temperature measurement sensitivity noncontacting measurement of a temperature of a target medium, comprising:
a radiation emission collector including a probe element configured for noncontacting collection of radiation emitted by the target medium, the radiation collected by the probe element having an intensity and occupying a range of wavelengths representing the temperature of the target medium; and
a radiation detector receiving a portion of the radiation collected by the probe element, the radiation emission collector directly coupled to the radiation detector to provide to it low loss transmission of the portion of the radiation collected, the radiation detector having a narrowband wavelength selective spectral response characteristic that enables the radiation detector in response to wavelengths of radiation within the range of wavelengths to provide a signal that is indicative of the temperature of the target medium, the radiation detector further having a field of view (FOV); and
the measurement system further having a zero offset calibration level that is below the low temperature measurement sensitivity of the measurement system, the zero offset calibration level being determined by providing a target medium having an emissivity greater than about 0.8, cooling the target medium, configuring the radiation detector so that the cooled target medium occupies the full FOV, and measuring the temperature of the cooled target medium.

* * * * *